United States Patent
Wang et al.

(10) Patent No.: US 11,053,207 B2
(45) Date of Patent: Jul. 6, 2021

(54) INDOLEAMINE-2,3-DIOXYGENASE INHIBITOR AND PREPARATION METHOD THEREFOR

(71) Applicant: SHANGHAI INSTITUTE OF ORGANIC CHEMISTRY, CHINESE ACADEMY OF SCIENCES, Shanghai (CN)

(72) Inventors: Zhaoyin Wang, Shanghai (CN); Wei Guo, Shanghai (CN); Jidong Zhu, Shanghai (CN)

(73) Assignee: Shanghai Institute of Organic Chemistry, Chinese Academy of Sciences, Xuhui District (CN)

( * ) Notice: Subject to any disclaimer, the term of this patent is extended or adjusted under 35 U.S.C. 154(b) by 607 days.

(21) Appl. No.: 15/510,984

(22) PCT Filed: Sep. 15, 2015

(86) PCT No.: PCT/CN2015/089666
§ 371 (c)(1),
(2) Date: Jul. 12, 2017

(87) PCT Pub. No.: WO2016/041489
PCT Pub. Date: Mar. 24, 2016

(65) Prior Publication Data
US 2019/0152932 A1    May 23, 2019

(30) Foreign Application Priority Data

Sep. 15, 2014   (CN) .................. 201410468433.X

(51) Int. Cl.
| | | |
|---|---|---|
| C07D 271/08 | (2006.01) |
| A61P 35/00 | (2006.01) |
| A61K 31/4245 | (2006.01) |
| A61P 37/00 | (2006.01) |
| A61P 25/00 | (2006.01) |
| A61P 37/02 | (2006.01) |
| A61P 25/28 | (2006.01) |
| A61P 25/22 | (2006.01) |
| A61P 25/24 | (2006.01) |

(52) U.S. Cl.
CPC ........ *C07D 271/08* (2013.01); *A61K 31/4245* (2013.01); *A61P 25/00* (2018.01); *A61P 25/22* (2018.01); *A61P 25/24* (2018.01); *A61P 25/28* (2018.01); *A61P 35/00* (2018.01); *A61P 37/00* (2018.01); *A61P 37/02* (2018.01)

(58) Field of Classification Search
CPC ... C07D 271/08; A61K 31/4245; A61P 25/24; A61P 25/28; A61P 37/00
See application file for complete search history.

(56) References Cited

U.S. PATENT DOCUMENTS

2008/0182882 A1   7/2008  Combs et al.

FOREIGN PATENT DOCUMENTS

| CN | 101212967 A | 7/2008 | |
|---|---|---|---|
| CN | 102164902 A | 8/2011 | |
| WO | 2007/075598 A2 | 7/2007 | |
| WO | WO-2010005958 A2 * | 1/2010 | ............... A61P 1/00 |
| WO | 2014/066834 A1 | 5/2014 | |

OTHER PUBLICATIONS

Meanwell, N.A., (J. Med. Chem. vol. 54 pp. 2529-2591 published 2011) (Year: 2011).*
Lucking, U. (Angew. Chem. Int. Ed vol. 52 pp. 9399-9408 published 2013) (Year: 2013).*
Meanwell (J. Med. Chem. vol. 54 pp. 2529-2591 published 2011). (Year: 2011).*
Lucking (Angew Chem Int Ed vol. 52 pp. 9399-9408. Published 2013). (Year: 2013).*
International Search Report dated Nov. 25, 2015 in PCT/CN2015/089666, 4 pages.

* cited by examiner

*Primary Examiner* — Theodore R. Howell
*Assistant Examiner* — George W Kosturko
(74) *Attorney, Agent, or Firm* — Kilpatrick Townsend and Stockton LLP

(57) ABSTRACT

Disclosed are a compound represented by general formula I and a preparation method therefor. The compound can be used as indoleamine-2,3-dioxygenase inhibitor to prepare medicines for preventing and/or treating indoleamine-2,3-dioxygenase-mediated diseases.

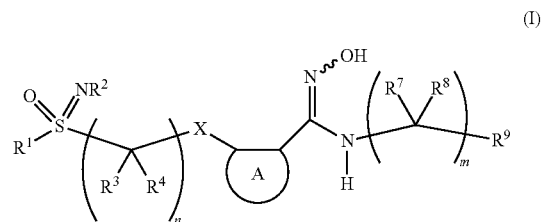

(I)

10 Claims, 1 Drawing Sheet

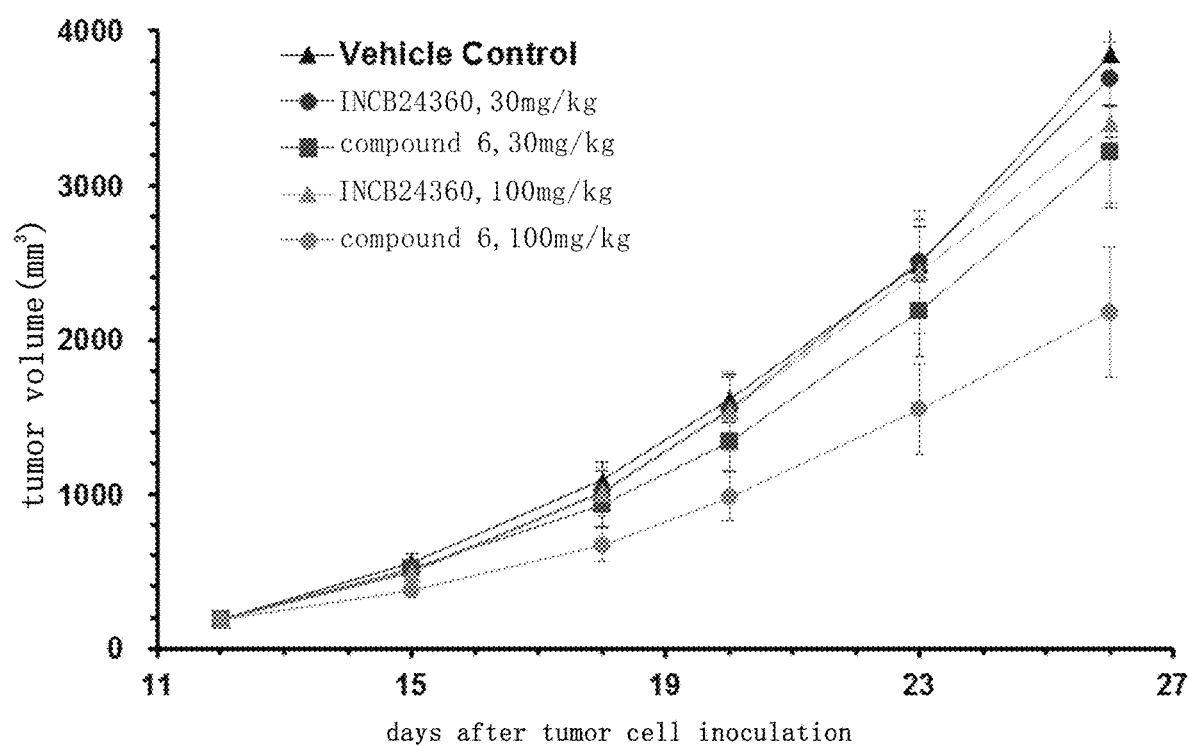

INDOLEAMINE-2,3-DIOXYGENASE INHIBITOR AND PREPARATION METHOD THEREFOR

TECHNICAL FIELD

The present invention relates to the field of pharmaceutical chemistry technology, in particular to a IDO inhibitor comprising sulfoxide imine and 1,2,5-oxadiazole structure and the preparation method thereof.

BACKGROUND ART

Indoleamine-2,3-dioxygenase (IDO) is a ferroheme-containing monomeric enzyme found in cells by the Hayaishi group for the first time in 1967. The cDNA encoded protein, consisting of 403 amino acids and having a molecular weight of 45 kDa, is a rate-limiting enzyme for the catabolism along the tryptophan-kynurenine pathway and widely expressed in a variety of mammalian tissues (Hayaishi O. et al *Science*, 1969, 164, 389-396). In the cells of cancer patients, IDO often plays an important physiological role in the induction of tumor microenvironment immune tolerance. The Tryptophan (Trp)-Kynurenine (Kyn) metabolic pathway mediated by IPO is involved in tumor immune escape, and IDO also plays an important role in the induction of tumor microenvironment immune tolerance.

Tryptophan is one of the important essential amino acids in mammals, which is needed to be largely intaken from food for the maintaining of cell activation and proliferation as well as the synthesis of proteins and some neurotransmitters. Therefore, its lacking will lead to the dysfunction of some important cells. IDO can catalyze the transformation of tryptophan into N-formyl kynurenine in vivo, degrading the content of tryptophan to result in the deficiency of tryptophan within body, thereby leading to tumorigenesis. In addition, immunohistochemical studies have shown that the kynurenine pathway can lead to the increase of an excitotoxin, quinolinic acid, and also cause a variety of severe human diseases such as Alzheimer's disease and other nervous system diseases (Guillemin G. J. et al *Neuropathol. and Appl. Neurobiol.* 2005, 31, 395-404).

There are primarily two tryptophan rate-limiting enzymes in mammals: tryptophan dioxygenase (TDO) and IDO. In 1937, Kotake. et al purified the protein from rabbit intestine and found for the first time that TDO was mainly expressed in mammalian liver, but no close relationship between TDO and the immune system has been found at present.

TDO can catalyze the kynurenine pathway to transform tryptophan into N-formyl kynurenine [Higuchi K. et al *J. Biochem*.1937, 25, 71-77; Shimizu T. et al *J. Biol. Chem.* 1978, 253, 4700-4706]. In 1978, an enzyme purified from the intestine of rabbit was identified as a dioxygenase (IDO) containing ferroheme, and IDO is the only enzyme outside the liver that can catalyze the oxidative cleavage of indole in the tryptophan molecule and catabolism along the tryptophan-kynurenine pathway. IDO is usually expressed in organs with more mucous membrane, such as, lung, small intestine and large intestine, rectum, spleen, kidney, stomach and brain, etc., and is widely distributed (Hayaishi O. et al, *Proceedings of the tenth FEBS meeting*, 1975, 131-144). In some special or pathological conditions, such as pregnancy, chronic infection, organ transplantation and cancer etc., IDO will have a remarkably increased expression level and take part in the mediation of local immunosuppression.

Studies have shown that in tumor microenvironment, IDO can inhibit local T cell immune response through the following ways: tryptophan depletion, toxic metabolism and induction of regulatory T cells proliferation. In many cases, IDO is over expressed in tumors, consuming local tryptophan and producing a large amount of kynurenine and other metabolites. In fact, in culture conditions without tryptophan or kynurenine, T cells can experience proliferation inhibition, decreased activity or even apoptosis. There is a quite sensitive set point for the tryptophan level in T cells. In the presence of IDO, tryptophan is consumed, as a result T cells are arrested in the middle of phase G1, and the proliferation of T cells and T cell immune response are thereby inhibited. O once the proliferation of T cells is stopped, the T cells may not be stimulated any more, which is the immune mechanism of IDO in vivo (Mellor A. et al *Biochem. Biophys. Res. Commun.* 2005, 338 (1): 20-24) (LeRond S. et al *J. Exp. Med.* 2002, 196 (4):447-457).

New IDO inhibitors are in need in the art.

SUMMARY OF THE INVENTION

The object of the present invention is to provide a new compound containing sulfoxide imine and 1,2,5-oxadiazole structure as an efficient IDO enzyme inhibitor.

The other object of the present invention is to provide a preparation method for the compound.

In the first aspect of the present invention, a compound represented by formula (I), or a pharmaceutically acceptable salt, stereoisomer or tautomer, or prodrug thereof is provided:

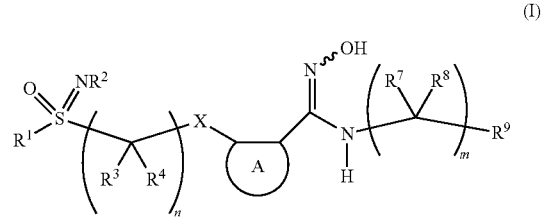

wherein, $R^7$ and $R^8$ are each independently H, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_3$-$C_{10}$ alkynyl, substituted or unsubstituted $C_6$-$C_{20}$ aryl, or substituted or unsubstituted $C_3$-$C_{14}$ heteroaryl; $R^7$ and $R^8$ can together form a three to eight membered ring or a three to eight membered heterocyclic ring, wherein the heteroatom can be sulfur, oxygen, NH or $NR^f$;

$R^9$ is $C_6$-$C_{20}$ aryl, five or six membered heteroaryl; $R^9$ can be substituted with one or more substituents selected from the group consisting of: halogen, $C_1$-$C_6$ alkyl, $C_1$-$C_6$ alkoxy, hydroxy, amino, nitro, aldehyde group, —$CF_3$, —CN, —$SF_5$, $NR^aR^b$, carboxyl, —$COR^a$, —$CO_2C_1$-$C_6$ alkyl, —$CONR^aR^b$, —$SO_2R^a$, —$SO_2NR^aR^b$, —$P(O)Me_2$, —$P(O)(OMe)_2$; wherein each $R^a$ and each $R^b$ are each independently H, substituted or unsubstituted $C_1$-$C_{10}$ alkyl, substituted or unsubstituted $C_3$-$C_{10}$ cycloalkyl, substituted or unsubstituted $C_2$-$C_{10}$ alkenyl, substituted or unsubstituted $C_6$-$C_{20}$ aryl, or substituted or unsubstituted $C_3$-$C_{14}$ heteroaryl; $R^a$ and $R^b$ can together form a three to eight membered ring or a four to eight membered heterocyclic ring, wherein the heteroatom can be sulfur, oxygen, NH or $NR^g$;

$R^2$ is H, —CN, —C(O)H or —C(O)$R^e$;

X is a single bond, O, S, NH or $NR^d$;

$R^3$ and $R^4$ are each H, substituted or unsubstituted $C_1$-$C_{10}$ alkyl; $R^3$ and $R^4$ can together form a three to eight membered ring or a three to eight membered heterocyclic ring, wherein the heteroatom can be sulfur, oxygen, NH or $NR^h$;

$R^1$, $R^d$, $R^e$, $R^f$, $R^g$, $R^h$ are each independently $C_1$-$C_{10}$ alkyl, $C_3$-$C_{10}$ cycloalkyl, $C_6$-$C_{20}$ aryl, or $C_3$-$C_{14}$ heteroaryl; $R^1$ can be substituted with one or more substituents selected from the group consisting of: halogen, hydroxy, amino, nitro, cyano, aldehyde group, carboxyl, alkoxy, —$CF_3$, —$SF_5$;

$R^1$ and $R^d$ can link to form a six to eight membered ring;

$R^1$ and $R^3$ can link to form a five to eight membered ring;

n is 2 to 8;

ring A is 1,2,5-oxadiazole ring;

m is 0 to 2.

In another preferred embodiment, the "substituted" means having one or more substituents selected from the group consisting of: halogen, hydroxy, —$NH_2$, nitro, —CN, C1-C4 alkyl, C1-C4 haloalkyl, C1-C4 alkoxy, C3-C6 cycloalkyl, C2-C4 alkenyl, C2-C4 alkynyl, phenyl, benzyl.

In another preferred embodiment, $R^2$ is H or —CN.

In another preferred embodiment, $R^3$ and $R^4$ are each independently H, substituted or unsubstituted $C_1$-$C_{10}$ alkyl; $R^3$ and $R^4$ can together form a three to eight membered ring or a three to eight membered heterocyclic ring, wherein the heteroatom can be sulfur, oxygen, NH or Me.

In another preferred embodiment, n is 2 to 6.

In another preferred embodiment, X is NH.

In another preferred embodiment, $R^3$ is H.

In another preferred embodiment, $R^4$ is H.

In another preferred embodiment, m is 0.

In another preferred embodiment, the compound is represented by the general formula (II),

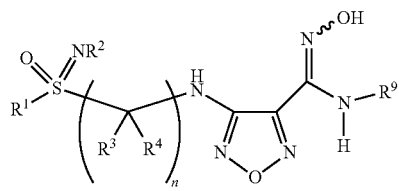

(II)

wherein, $R^9$ is $C_6$-$C_{20}$ aryl, five or six membered heteroaryl; $R^9$ can be substituted with one or more substituents selected from the group consisting of: halogen, $C_1$-$C_6$ alkyl, $C_1$-$C_6$ alkoxy, hydroxy, amino, nitro, aldehyde group, —$CF_3$, —CN, —$SF_5$, $NR^aR^b$, carboxyl, —$COR^a$, —$CO_2C_1$-$C_6$ alkyl, —$CONR^aR^b$, —$SO_2R^a$, —$SO_2NR^aR^b$;

wherein, the definition of $R^a$, $R^b$, $R^3$, $R^4$, $R^a$ is described above;

$R^2$ is H or —CN;

n is 2-6.

In another preferred embodiment, $R^1$ is $C_1$-$C_{10}$ alkyl, $C_3$-$C_{10}$ cycloalkyl, $C_6$-$C_{20}$ aryl, or $C_3$-$C_{10}$ heteroaryl; $R^1$ can be substituted with one or more halogen.

In another preferred embodiment, $R^1$ is $C_1$-$C_{10}$ alkyl;

$R^2$ is H or —CN;

$R^3$ and $R^4$ are each independently H;

$R^9$ is $C_6$-$C_{10}$ aryl, five or six membered heteroaryl; $R^9$ can be substituted with one or more substituents selected from the group consisting of: halogen, $C_1$-$C_6$ alkyl, $C_1$-$C_6$ alkoxy, hydroxy, amino, nitro, aldehyde group, —$CF_3$, —CN, —$SF_5$.

In another preferred embodiment, $R^1$ is $C_1$-$C_4$ alkyl;

$R^9$ is $C_6$-$C_{10}$ aryl, five or six membered heteroaryl; $R^9$ can be substituted with one or more substituents selected from the group consisting of: halogen, $C_1$-$C_6$ alkyl, $C_1$-$C_6$ alkoxy, hydroxy, —$CF_3$, —CN, —$SF_5$. In another preferred embodiment, the prodrug of the compound of general formula I is represented by the general formula (III),

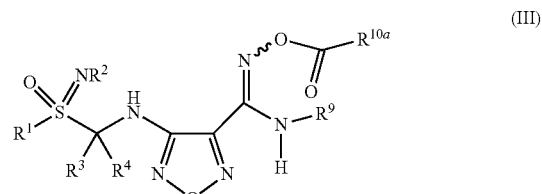

(III)

wherein, the definition of $R^1$, $R^2$, $R^3$, $R^4$ and $R^9$ is described above;

$R^{10a}$ is substituted or unsubstituted $C_6$-$C_{20}$ aryl, substituted or unsubstituted five or six membered heteroaryl, substituted or unsubstituted $C_1$-$C_{12}$ alkyl, substituted or unsubstituted $C_1$-$C_{12}$ alkoxy, substituted or unsubstituted $C_3$-$C_{12}$ cycloalkyl, $C_3$-$C_{12}$ cycloalkoxy, $NR^aR^b$; wherein, the definition of $R^a$, $R^b$ is described above;

wherein, the term "substituted" means having one or more substituents selected from the group consisting of: halogen, hydroxy, —$NH_2$, nitro, —CN, C1-C4 alkyl, C1-C4 haloalkyl, C1-C4 alkoxy, C3-C6 cycloalkyl, C2-C4 alkenyl, C2-C4 alkynyl, phenyl, benzyl.

In another preferred embodiment, X, $R^1$, $R^2$, $R^3$, $R^4$, $R^7$, $R^8$, $R^9$, $R^{10a}$ and ring A are each independently the corresponding substituents in each specific compound of formula I, II and III prepared in the examples.

In another preferred embodiment, the compound is:

(±)(Z)—N-(3-bromo-4-fluorophenyl)-N'-hydroxy-4-((2-(thio-methyl sulfoxide imine) ethyl) amino)-1,2,5-oxadiazole-3-carboxamidine;

(+)(Z)—N-(3-bromo-4-fluorophenyl)-N'-hydroxy-4-((2-(thio-methyl sulfoxide imine) ethyl)amino)-1,2,5-oxadiazole-3-carboxamidine;

(−)(Z)—N-(3-bromo-4-fluorophenyl)-N'-hydroxy-4-((2-(thio-methyl sulfoxide imine) ethyl)amino)-1,2,5-oxadiazole-3-carboxamidine;

(±)(Z)—N-(3-bromo-4-fluorophenyl)-N'-hydroxy-4-((3-(thio-methyl sulfoxide imine) propyl)amino)-1,2,5-oxadiazole-3-carboxamidine;

(+)(Z)—N-(3-bromo-4-fluorophenyl)-N'-hydroxy-4-((3-(thio-methyl sulfoxide imine) propyl)amino)-1,2,5-oxadiazole-3-carboxamidine;

(−)(Z)—N-(3-bromo-4-fluorophenyl)-N'-hydroxy-4-((3-(thio-methyl sulfoxide imine) propyl)amino)-1,2,5-oxadiazole-3-carboxamidine;

(±)(Z)—N-(3-bromo-4-fluorophenyl)-N'-hydroxy-4-((4-(thio-methyl sulfoxide imine) butyl)amino)-1,2,5-oxadiazole-3-carboxamidine;

(+)(Z)—N-(3-bromo-4-fluorophenyl)-N'-hydroxy-4-((4-(thio-methyl sulfoxide imine) butyl)amino)-1,2,5-oxadiazole-3-carboxamidine;

(−)(Z)—N-(3-bromo-4-fluorophenyl)-N'-hydroxy-4-((4-(thio-methyl sulfoxide imine) butyl)amino)-1,2,5-oxadiazole-3-carboxamidine;

(±)(Z)—N-(4-fluoro-3-(trifluoromethyl)phenyl)-N'-hydroxy-4-((4-(thio-methyl sulfoxide imine)butyl)amino)-1,2,5-oxadiazole-3-carboxamidine;

(+)(Z)—N-(4-fluoro-3-(trifluoromethyl)phenyl)-N'-hydroxy-4-((4-(thio-methyl sulfoxide imine)butyl)amino)-1,2,5-oxadiazole-3-carboxamidine;

(−)(Z)—N-(4-fluoro-3-(trifluoromethyl)phenyl)-N'-hydroxy-4-((4-(thio-methyl sulfoxide imine)butyl)amino)-1,2,5-oxadiazole-3-carboxamidine;

(±)(Z)—N'-hydroxy-4-((4-(thio-methyl sulfoxide imine) butyl) amino)-N-(3-(trifluoromethyl)phenyl)-1,2,5-oxadiazole-3-carboxamidine;

(+)(Z)—N'-hydroxy-4-((4-(thio-methyl sulfoxide imine) butyl) amino)-N-(3-(trifluoromethyl)phenyl)-1,2,5-oxadiazole-3-carboxamidine;

(−)(Z)—N'-hydroxy-4-((4-(thio-methyl sulfoxide imine) butyl) amino)-N-(3-(trifluoromethyl)phenyl)-1,2,5-oxadiazole-3-carboxamidine;

(±)(Z)—N-(3-bromo-4-fluorophenyl)-N'-hydroxy-4-((2-(thio-methyl sulfoxide cyano amine)ethyl)amino)-1,2,5-oxadiazole-3-carboxamidine;

(+)(Z)—N-(3-bromo-4-fluorophenyl)-N'-hydroxy-4-((2-(thio-methyl sulfoxide cyano amine)ethyl)amino)-1,2,5-oxadiazole-3-carboxamidine; or (−)(Z)—N-(3-bromo-4-fluorophenyl)-N'-hydroxy-4-((2-(thio-methyl sulfoxide cyano amine)ethyl)amino)-1,2,5-oxadiazole-3-carboxamidine;

(±)(Z)—N-(3-bromo-4-fluorophenyl)-N'-hydroxy-4-((2-(thio-phenyl sulfoxide imine) ethyl)amino)-1,2,5-oxadiazole-3-carboxamidine;

(+)(Z)—N-(3-bromo-4-fluorophenyl)-N'-hydroxy-4-((2-(thio-phenyl sulfoxide imine) ethyl)amino)-1,2,5-oxadiazole-3-carboxamidine;

(−) (Z)—N-(3-bromo-4-fluorophenyl)-N'-hydroxy-4-((2-(thio-phenyl sulfoxide imine) ethyl)amino)-1,2,5-oxadiazole-3-carboxamidine (±)(Z)—N-(3-pentafluoride thiophenyl)-N'-hydroxy-4-((2-(thio-methyl sulfoxide imine) ethyl)amino)-1,2,5-oxadiazole-3-carboxamidine;

(+)(Z)—N-(3-pentafluoride thiophenyl)-N'-hydroxy-4-((2-(thio-methyl sulfoxide imine) ethyl)amino)-1,2,5-oxadiazole-3-carboxamidine;

(−) (Z)—N-(3-pentafluoride thiophenyl)-N'-hydroxy-4-((2-(thio-methyl sulfoxide imine) ethyl)amino)-1,2,5-oxadiazole-3-carboxamidine;

(±)(Z)—N-(3-bromo-4-fluorophenyl)-N'-hydroxy-4-((3-(thio-methyl sulfoxide cyano amine)propyl)amino)-1,2,5-oxadiazole-3-carboxamidine;

(+)(Z)—N-(3-bromo-4-fluorophenyl)-N'-hydroxy-4-((3-(thio-methyl sulfoxide cyano amine)propyl)amino)-1,2,5-oxadiazole-3-carboxamidine;

(−)(Z)—N-(3-bromo-4-fluorophenyl)-N'-hydroxy-4-((3-(thio-methyl sulfoxide cyano amine)propyl)amino)-1,2,5-oxadiazole-3-carboxamidine;

(±)(Z)—N-(3-chloro-4-fluorophenyl)-N'-hydroxy-4-((3-(thio-methyl sulfoxide cyano amine)propyl)amino)-1,2,5-oxadiazole-3-carboxamidine;

(+)(Z)—N-(3-chloro-4-fluorophenyl)-N'-hydroxy-4-((3-(thio-methyl sulfoxide cyano amine)propyl)amino)-1,2,5-oxadiazole-3-carboxamidine;

(−)(Z)—N-(3-chloro-4-fluorophenyl)-N'-hydroxy-4-((3-(thio-methyl sulfoxide cyano amine)propyl)amino)-1,2,5-oxadiazole-3-carboxamidine;

(±)(Z)—N-(3-bromo-4-fluorophenyl)-N'-hydroxy-4-((4-(thio-methyl sulfoxide cyano amine)butyl)amino)-1,2,5-oxadiazole-3-carboxamidine;

(+)(Z)—N-(3-bromo-4-fluorophenyl)-N'-hydroxy-4-((4-(thio-methyl sulfoxide cyano amine)butyl)amino)-1,2,5-oxadiazole-3-carboxamidine;

(−)(Z)—N-(3-bromo-4-fluorophenyl)-N'-hydroxy-4-((4-(thio-methyl sulfoxide cyano amine)butyl)amino)-1,2,5-oxadiazole-3-carboxamidine;

(±)(Z)—N-(3-chloro-4-fluorophenyl)-N'-hydroxy-4-((4-(thio-methyl sulfoxide cyano amine)butyl)amino)-1,2,5-oxadiazole-3-carboxamidine;

(+)(Z)—N-(3-chloro-4-fluorophenyl)-N'-hydroxy-4-((4-(thio-methyl sulfoxide cyano amine)butyl)amino)-1,2,5-oxadiazole-3-carboxamidine;

(−)(Z)—N-(3-chloro-4-fluorophenyl)-N'-hydroxy-4-((4-(thio-methyl sulfoxide cyano amine)butyl)amino)-1,2,5-oxadiazole-3-carboxamidine;

(±)(Z)—N-(3-bromo-4-fluorophenyl)-N'-hydroxy-4-((2-(thio-methyl sulfoxide cyano amine)ethyl)amino)-1,2,5-oxadiazole-3-acetate;

(+)(Z)—N-(3-bromo-4-fluorophenyl)-N'-hydroxy-4-((2-(thio-methyl sulfoxide cyano amine)ethyl)amino)-1,2,5-oxadiazole-3-acetate;

(−)(Z)—N-(3-bromo-4-fluorophenyl)-N'-hydroxy-4-((2-(thio-methyl sulfoxide cyano amine)ethyl)amino)-1,2,5-oxadiazole-3-acetate;

(±)(Z)—N-(3-bromo-4-fluorophenyl)-N'-hydroxy-4-((2-(thio-methyl sulfoxide cyano amine)ethyl)amino)-1,2,5-oxadiazole-3-(3, 3-dimethyl)butyrate;

(+)(Z)—N-(3-bromo-4-fluorophenyl)-N'-hydroxy-4-((2-(thio-methyl sulfoxide cyano amine)ethyl)amino)-1,2,5-oxadiazole-3-(3, 3-dimethyl)butyrate;

(−)(Z)—N-(3-bromo-4-fluorophenyl)-N'-hydroxy-4-((2-(thio-methyl sulfoxide cyano amine)ethyl)amino)-1,2,5-oxadiazole-3-(3, 3-dimethyl)butyrate;

(±)(Z)—N-(3-bromo-4-fluorophenyl)-N'-hydroxy-4-((2-(thio-methyl sulfoxide cyano amine)ethyl)amino)-1,2,5-oxadiazole-3-isobutyrate;

(+)(Z)—N-(3-bromo-4-fluorophenyl)-N'-hydroxy-4-((2-(thio-methyl sulfoxide cyano amine)ethyl)amino)-1,2,5-oxadiazole-3-isobutyrate;

(−)(Z)—N-(3-bromo-4-fluorophenyl)-N'-hydroxy-4-((2-(thio-methyl sulfoxide cyano amine)ethyl)amino)-1,2,5-oxadiazole-3-isobutyrate;

(±)(Z)—N-(3-bromo-4-fluorophenyl)-N'-hydroxy-4-((2-(thio-methyl sulfoxide cyano amine)ethyl)amino)-1,2,5-oxadiazole-3-trimethyl acetate;

(+)(Z)—N-(3-bromo-4-fluorophenyl)-N'-hydroxy-4-((2-(thio-methyl sulfoxide cyano amine)ethyl)amino)-1,2,5-oxadiazole-3-trimethyl acetate; or (−)(Z)—N-(3-bromo-4-fluorophenyl)-N'-hydroxy-4-((2-(thio-methyl sulfoxide cyano amine)ethyl)amino)-1,2,5-oxadiazole-3-trimethyl acetate.

In another preferred embodiment, the compound is the compound 1-15 prepared in the examples.

In another preferred embodiment, the compound is a racemate.

In another preferred embodiment, the compound is an enantiomer.

In another preferred embodiment, the pharmaceutically acceptable salt is selected from the group consisting of: hydrochloride, hydrobromide, sulfates, phosphates, methanesulfonates, trifluoromethanesulfonates, benzenesulfonates, p-toluenesulfonates (toluenesulfonate), 1-naphthalenesulfonate, 2-naphthalenesulfonate, acetate, trifluoroacetate, malate, tartrate, citrate, lactate, oxalate, succinate, fumarate, maleate, benzoate, salicylate, phenylacetate, mandelate.

In the second aspect of the present invention, a method for preparing the compound of formula I according to the first aspect is provided, comprising the following steps:

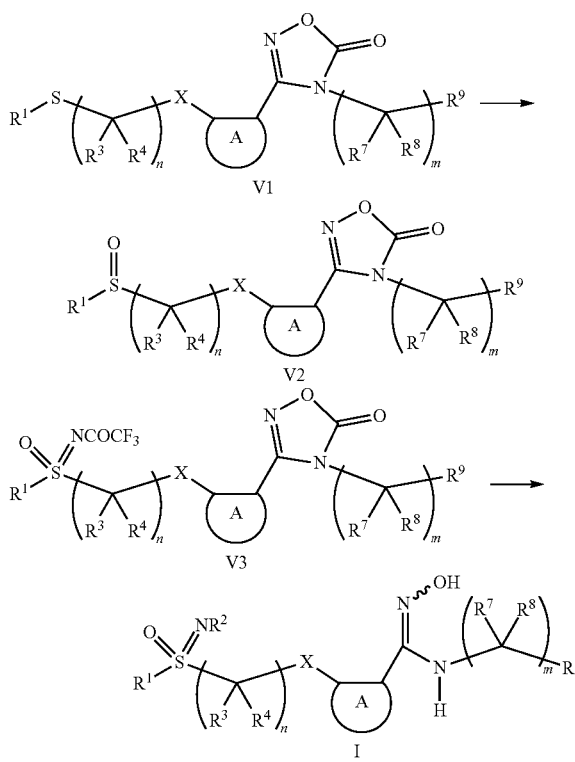

(a) reacting compound V1 with a peroxide, magnesium monoperoxyphthalate (MMPP), to obtain compound V2;

(b) reacting compound V2 with trifluoroacetamide, to obtain compound $V_3$;

(c) in the presence of sodium hydroxide (e.g., aqueous sodium hydroxide), subjecting compound V3 to a ring-open reaction, and meantime removing the trifluoroacetylamino group, to obtain the final product, i.e., the compound of formula I, wherein, the definition of $R^1$, $R^2$, $R^3$, $R^4$, $R^7$, $R^8$, $R^9$, n, m, X and ring A is described above.

In the present invention, compound V1 is obtained using propylene cyanide as the starting material through a series of oxidation, addition, cyclization, diazotization, substitution and the like.

In the third aspect of the present invention, a use of the compound of formula I according to the first aspect is provided, wherein the use is for:

(i) the preparation of an indoleamine-2,3-dioxygenase inhibitor;

(ii) the preparation of a medicament for the prevention and/or treatment of indoleamine-2,3-dioxygenase-mediated diseases; or (iii) the preparation of an anti-inflammatory medicament.

In another preferred embodiment, said indoleamine-2,3-dioxygenase-mediated diseases are diseases characterized by the pathologic characteristics of IDO-mediated tryptophan metabolic pathways.

In another preferred embodiment, said indoleamine-2,3-dioxygenase-mediated diseases are cancer, eye diseases, psychological disorders, depression, anxiety disorders, senile dementia and/or autoimmune diseases.

In another preferred embodiment, said cancer includes, but is not limited to: colon cancer, breast cancer, stomach cancer, lung cancer, colorectal cancer, pancreatic cancer, ovarian cancer, prostate cancer, kidney cancer, liver cancer, brain cancer, melanoma, multiple myeloma, chronic myeloid leukemia, blood tumor, lymphoid tumor, including metastatic lesions in other tissues or organs that are away from the primary site of tumor.

In the fourth aspect of the present invention, a pharmaceutical composition is provided, wherein the pharmaceutical composition comprises:

the compound represented by formula (I), or a pharmaceutically acceptable salt, stereoisomer or tautomer, or prodrug thereof according to the first aspect; and a pharmaceutically acceptable carrier.

In the fifth aspect of the present invention, a pharmaceutical composition is provided, wherein the pharmaceutical composition comprises:

the compound represented by formula (I), or a pharmaceutically acceptable salt, stereoisomer or tautomer, or prodrug thereof according to the first aspect; and an antineoplastic agent.

In another preferred embodiment, the antineoplastic agent includes, but is not limited to, immunotherapeutic drugs for cancer: PD-1 antibody, CTLA-4 antibody, PD-L1 antibody, PD-L2 antibody, any other chemotherapeutic agent or targeted therapy agent.

In the sixth aspect of the present invention, a method for the prevention and/or treatment of an indoleamine-2,3-dioxygenase-mediated disease is provided, comprising the step of administering to a patient the compound of Formula I according to the first aspect or the pharmaceutical composition according to the fourth or fifth aspect.

In another preferred embodiment, the indoleamine-2,3-dioxygenase-mediated disease is cancer, and the method further comprises the step of administering to the patient an additional anti-cancer agent (also known as an antineoplastic agent, which is as described above).

The compound of formula I of the present invention has various pharmacological activities such as anti-tumor, treatment of neurodegenerative diseases (Alzheimer's disease), anti-inflammation and the like.

It is to be understood that within the scope of the present invention, each foregoing technical feature of the present invention and each technical feature described in detail below (e.g., examples) may be combined with each other to form a new or preferred technical solution, which is not elaborated herein for the sake of brevity.

DESCRIPTION OF DRAWINGS

FIG. 1 shows that compound 6 of the present invention has a more potent inhibitory effect on tumor growth than the control compound, INCB2436, in a mouse primary rectal cancer tumor CT-26 model.

DETAILED DESCRIPTION OF THE INVENTION

Through a long-term and in-depth study, the inventors have, for the first time, unexpectedly found a new compound containing sulfoxide imine and 1,2,5-oxadiazole structure. The compounds can be used as an efficient IDO enzyme inhibitor for the prevention and/or treatment of indoleamine-2,3-dioxygenase-mediated diseases, and also can be used as an anti-inflammatory drug. Based on the above findings, the present invention was completed.

Definition

The term "alkyl" refers to a monovalent saturated aliphatic hydrocarbyl having 1-10 carbon atoms, comprising straight or branched hydrocarbyl groups such as methyl (i.e., $CH_3$—), ethyl (i.e., $CH_3CH_2$—), n-propyl (i.e., $CH_3CH_2CH_2$—), isopropyl (i.e., $(CH_3)_2CH$—), n-butyl (i.e., $CH_3CH_2CH_2CH_2$—), isobutyl (i.e., $(CH_3)_2CHCH_2$—), sec-butyl (i.e., $(CH_3)(CH_3CH_2)CH$—), tertiary butyl (i.e., $(CH_3)_3C$—), n-pentyl (i.e., $CH_3CH_2CH_2CH_2CH_2$—), neopentyl (i.e., $(CH_3)_3CCH_2$—). In the present invention, the term includes substituted or unsubstituted alkyl.

As used herein, the term "substituted or unsubstituted" means that a group can be unsubstituted, or H in the group is substituted with one or more (preferably, 1-6, more preferably, 1-3) substituents.

As used herein, the term "substitution" or "substituted" refers to a group having one or more (preferably, 1-6, more preferably, 1-3) substituents selected from the group consisting of: halogen, hydroxy, —$NH_2$, nitro, —CN, C1-C4 alkyl, C1-C4 haloalkyl, C1-C4 alkoxy, C3-C6 cycloalkyl, C2-C4 alkenyl, C2-C4 alkynyl, phenyl, benzyl.

As used herein, the term "cycloalkyl" refers to substituted or unsubstituted C3-C12 cycloalkyl.

As used herein, the term "alkoxy" refers to —O-alkyl, wherein the alkyl can be saturated or unsaturated, and can be branched, straight, or cyclic. Preferably, alkoxy has 1-10 carbon atoms, more preferably, 1-6 carbon atoms. Representative examples include, but are not limited to: methoxy, ethoxy, propoxy.

As used herein, the term "aryl" refers to a monovalent aromatic carbocyclic group having 6-20 (more preferably, 6-14) carbon atoms, which has a monocyclic (e.g., phenyl) or a fused ring (e.g., naphthyl or anthryl), and if the connection point is on an aromatic carbon atom, the fused ring may be non-aromatic (such as 2-benzoxazolone, 2H-1,4-benzoxazin-3 (4H)-one-7-yl and the like). Preferred aryls include phenyl and naphthyl. The term includes the substituted or unsubstituted form, wherein the definition of the substituents is as described above.

As used herein, the term "alkenyl" refers to an alkenyl having 2-10 (such as 2-6 or 2-4) carbon atoms, and having at least 1 (such as 1-2) unsaturated olefinic bond (>C=C<). Examples of such groups are vinyl, allyl, but-3-enyl. As used herein, the term "cycloalkyl" refers to a cyclic alkyl group with 3 to 10 carbon atoms having monocyclic or polycyclic (including fused systems, bridging systems and spiro ring systems). In the fused ring systems, one or more rings may be cycloalkyl, heterocyclic, aryl or heteroaryl, as long as the linker site is through the ring of the cycloalkyl group. Examples of suitable cycloalkyl groups include: such as, adamantyl, cyclopropyl, cyclobutyl, cyclopentyl and cyclooctyl.

As used herein, the term "halo" or "halogen" refers to F, Cl, Br, and I.

As used herein, the term "heteroaryl" refers to an aromatic group having 1 to 10 carbon atoms and 1-4 heteroatoms selected from O, N and S in the ring, and such heteroaryl can be monocyclic (e.g., pyridyl or furanyl) or a fused ring (e.g., indolizinyl or benzothienyl), wherein the fused ring can be non-aromatic and/or which contains a heteroatom, as long as the linker site is through an aromatic heteroaryl atom. In an example, the ring atoms N and/or S in the heteroaryl are optionally oxidized to N-oxide (N—O), sulfinyl or sulfonyl. Preferably, the heteroaryl includes pyridyl, pyrrolyl, indolyl, thienyl and furyl. The term includes substituted or unsubstituted heteroaryl.

As used herein, the term "substituted heteroaryl" refers to a heteroaryl substituted with 1-5, preferably 1-3, more preferably 1-2 substituents, wherein the substituents are selected from the same substituents as defined for the substituted aryl.

As used herein, the term "heterocyclic ring" or "heterocyclic" or "heterocycloalkyl" or "heterocyclyl" refers to a saturated, partially saturated or unsaturated group (but not aromatic), having a monocyclic or fused ring (including a bridged ring system and a spiro ring system with 1-10 carbon atoms and 1-4 heteroatoms selected from N, S or O in the ring, and in fused ring systems, one or more rings can be cycloalkyl, aryl or heteroaryl, as long as the linker site is through a non-aromatic ring. In an example, the N atom and/or sulfur atom of the heterocyclic group are optionally oxidized to provide an N-oxide, sulfinyl and sulfonyl moiety.

As used herein, the term "substituted heterocyclic" or "substituted heterocycloalkyl" or "substituted heterocyclyl" refers to a heterocyclic group substituted with 1-5 (e.g., 1-3) substituents, wherein the substituents are the same as the substituents defined for the substituted cycloalkyl.

As used herein, the term "stereoisomer" refers to chirally different compounds with one or more stereogenic centers. The stereoisomer includes enantiomers and diastereomers.

As used herein, the term "tautomer" refers to an alternative form of a compound with different proton positions, such as enol-ketone and imine-enamine tautomers, or tautomeric forms of heteroaryl, wherein the heteroaryl includes ring atoms linked to the —NH— moiety and the =N— moiety of the ring, such as pyrazole, imidazole, benzimidazole, triazole and tetrazole.

"Prodrug" refers to any derivatives of the compounds in the examples which, when administered to a subject, can provide, directly or indirectly, the compounds of the examples or their active metabolites or residues. Particularly preferred derivatives and prodrugs are those that, when administered to a subject, can increase bioavailability of the compounds of the examples (e.g., orally administered compounds are more easily absorbed into the blood) or increase delivery of the parent compounds to a biota chamber (such as brain or lymphatic system) compared with the parent species. Prodrugs include the ester form of the compounds of the present invention.

The Compounds of the Present Invention

As used herein, the phrase "the compound(s) of the present invention" refers to the compound of formula I (or II), or a racemate, stereoisomer or tautomer, or pharmaceutically acceptable salt thereof. It is to be understood that, the phrase further comprises a compound of formula III, or a racemate, stereoisomer or tautomer, or pharmaceutically acceptable salt thereof.

The present invention relates to a racemic mixture of these compounds, a mixture enriched with any of the enantiomers, as well as any of the isolated enantiomers. For the scope of the present invention, it is to be understood that a racemic mixture refers to a mixture of two R and S enantiomers of 50%: 50%. The isolated enantiomers are to be understood as pure enantiomers (i.e., 100%) or a mixture highly enriched with a certain enantiomer (purity ≥98%, ≥95%, ≥93%, ≥90%, ≥88%, ≥85%, ≥80%).

Typically, a compound of formula I or a pharmaceutically acceptable salt, stereoisomer or tautomer, prodrug thereof is provided,

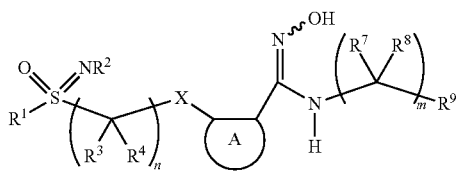

wherein,

R$^7$ and R$^g$ are each independently H, substituted or unsubstituted C$_1$-C$_{10}$ alkyl, substituted or unsubstituted C$_3$-C$_{10}$ cycloalkyl, substituted or unsubstituted C$_2$-C$_{10}$ alkenyl, substituted or unsubstituted C$_3$-C$_{10}$ alkynyl, substituted or unsubstituted C$_6$-C$_{20}$ aryl, or substituted or unsubstituted C$_3$-C$_{14}$ heteroaryl; R$^7$ and R$^8$ can together form a three to eight membered ring or a three to eight membered heterocyclic ring, wherein the heteroatom can be sulfur, oxygen, NH or NR$^f$;

R$^9$ is C$_6$-C$_{20}$ aryl, five or six membered heteroaryl; R$^9$ can be substituted with one or more substituents selected from the group consisting of: halogen, C$_1$-C$_6$ alkyl, C$_1$-C$_6$ alkoxy, hydroxy, amino, nitro, aldehyde group, —CF$_3$, —CN, —SF$_5$, NR$^a$R$^b$, carboxyl, —COR$^a$, —CO$_2$C$_1$-C$_6$ alkyl, —CONR$^a$R$^b$, —SO$_2$R$^a$, —SO$_2$NR$^a$R$^b$, —P(O)Me$_2$, —P(O)(OMe)$_2$; wherein each R$^a$ and each R$^b$ are each independently H, substituted or unsubstituted C$_1$-C$_{10}$ alkyl, substituted or unsubstituted C$_3$-C$_{10}$ cycloalkyl, substituted or unsubstituted C$_2$-C$_{10}$ alkenyl, substituted or unsubstituted C$_6$-C$_{20}$aryl, or substituted or unsubstituted C$_3$-C$_{14}$ heteroaryl; R$^a$ and R$^b$ can together form a three to eight membered ring or a four to eight membered heterocyclic ring, wherein the heteroatom can be sulfur, oxygen, NH or NR$^g$;

R$^2$ is H, —CN, —C(O)H or —C(O)R$^e$;

X is a single bond, O, S, NH or NR$^d$;

R$^3$ and R$^4$ are each independently H, substituted or unsubstituted C$_1$-C$_{10}$ alkyl; R$^3$ and R$^4$ can together form a three to eight membered ring or three to eight membered heterocyclic ring, wherein the heteroatom can be sulfur, oxygen, NH or NR$^h$;

R$^1$, R$^d$, R$^e$, R$^f$, R$^g$, R$^h$ are each independently C$_1$-C$_{10}$ alkyl, C$_3$-C$_{10}$ cycloalkyl, C$_6$-C$_{20}$ aryl, or C$_3$-C$_{14}$ heteroaryl; R$^1$ can be substituted with one or more substituents selected from the group consisting of: halogen, hydroxy, amino, nitro, cyano, aldehyde group, carboxyl, alkoxy, —CF$_3$, —SF$_5$;

R$^1$ and R$^d$ can link to form a six to eight membered ring;
R$^1$ and R$^3$ can link to form a five to eight membered ring;
n is 2 to 8;
ring A is 1,2,5-oxadiazole ring;
m is 0 to 2.

In another preferred embodiment, the compound of formula I is:

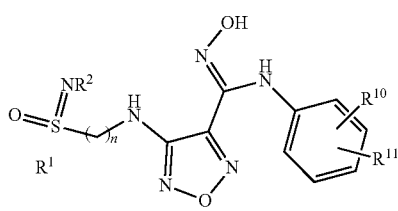

wherein R$^1$ is C$_1$-C$_{10}$ alkyl, C$_3$-C$_{10}$ cycloalkyl, C$_1$-C$_{10}$ alkenyl, aryl, or heteroaryl, can be substituted with one or more halogens.

R$^2$ is H or —CN;

R$^{10}$ and R$^{11}$ are each independently H, halogen, C$_1$-C$_6$ alkyl, C$_1$-C$_6$ alkoxy, C$_2$-C$_6$ alkynyl, hydroxy, amino, nitro, cyano, aldehyde group, —CF$_3$, —CN, —SF$_5$, NR$^a$R$^b$, carboxyl, —CO$_2$C$_1$-C$_6$ alkyl, —CONR$^a$R$^b$, —SO$_2$R$^a$, SO$_2$NR$^a$R$^b$ substituents; the definition of R$^a$ and R$^b$ is described above;

n is 1 to 8.

In another preferred embodiment, a prodrug of formula III is provided by the present invention:

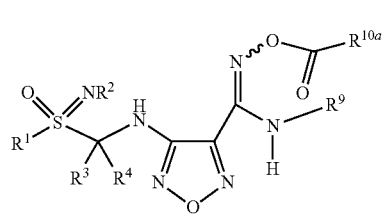

wherein the definition of each group is described above.

In the case where the compounds of the present invention have stereoisomers, the present invention comprises all stereoisomers of the compounds.

In the case where the compounds of the present invention have tautomers, the present invention comprises all tautomers of the compounds.

The present invention also includes a deuterium compound in which any one or more of the hydrogen atoms in the compounds are substituted with its stable isotope deuterium.

Pharmaceutical Compositions

A pharmaceutical composition is also provided by the present invention, comprising an active ingredient within a safe and effective dosage, and a pharmaceutically acceptable carrier.

The "active ingredient" in the present invention refers to the compound of formula I or a pharmaceutically acceptable salt, stereoisomer or tautomer, prodrug thereof according to the present invention.

The "active ingredient" and pharmaceutical compositions in the present invention can be used as an IDO inhibitor. In another preferred embodiment, for the preparation of a medicament for the prevention and/or treatment of tumors. In another preferred embodiment, for the preparation of a medicament for the prevention and/or treatment of IDO mediated diseases.

"a safe and effective dosage" means: the amount of the active ingredient is sufficient to significantly ameliorate the condition without causing serious side effects. Generally, the pharmaceutical composition contains 1-2000 mg of the active ingredient/dose, more preferably 10 to 200 mg of the active ingredient/dose. Preferably, the "one dose" is a tablet.

"Pharmaceutically acceptable carrier" refers to: one or more compatible solid or liquid fillers or gel materials that are suitable for human use and must have sufficient purity and sufficiently low toxicity. "Compatible" herein means that each component in the composition can be admixed with the active ingredients of the present invention and with each other without significantly reducing the efficacy of the active ingredients.

The compounds of the preferred embodiments of the present invention may be administered as a separate active agent or in combination with one or more other agents for the treatment of cancer. It is effective to use the compounds of the preferred embodiments of the present invention in combination with known therapeutic agents and anti-cancer agents, and combinations of currently known compounds and other anti-cancer agents or chemotherapeutic agents are within the scope of the preferred embodiments. Examples of such agents can be found in *Cancer Principles and Practice of Oncology*, V. T. Devita and S. Hellman (editor), 6th edition (Feb. 15, 2001), published by Lippincott Williams & Wilkins. Based on the particular properties of the drugs and the cancer involved, the skilled in the art can identify effective pharmaceutical combinations. Such anti-cancer agents include, but are not limited to: estrogen receptor modulators, androgen receptor modulators, retinol receptor modulators, cytotoxic/cell growth inhibitors, antiproliferative agents, isopentenyl protein transferase inhibitors, HMG-CoA reductase inhibitors and other angiogenesis inhibitors, cell proliferation and survival signal inhibitors, apoptosis inducers and agents that interfere with cell cycle checkpoint, CTLA4 antibody, PD-1 antibody, PD-L1 antibody, and the like. The compounds of the preferred embodiment are also effective when administered in combination with radiation therapy.

In general, the compounds of the preferred embodiments will be administered in a therapeutically effective amount by any of the acceptable modes for an agent having similar effects. The actual usage amounts of the compounds (i.e., the active ingredients) of the preferred embodiments are determined based on a number of factors such as the severity of the disease to be treated, the age and relative health of the patient, the potency of the compound to be used, the route and form of administration, and other factors. The medicament may be administered multiple times a day, preferably once or twice a day. All of these factors are within the scope of the attending physician's consideration.

For the purposes of the preferred embodiment, the therapeutically effective dosage may generally be a daily total dosage administered to a patient in a single or multiple applications, for example, about 0.001 to 1000 mg/kg body weight per day, preferably about 1.0 to 30 mg/kg body weight. A dosage unit composition may contain a dose factor to form a daily dose. The choice of dosage form depends on various factors such as the mode of administration and the bioavailability of the drug substance. In general, the compounds of the preferred embodiments may be administered as a pharmaceutical composition by any of the administration routes selected from the group consisting of: oral administration, systemic administration (e.g., transdermal, intranasal or via suppositories), or parenteral administration (e.g., intramuscular, intravenous or subcutaneous). The preferred mode of administration is oral, and the convenient daily dose can be adjusted according to the degree of bitterness. The compositions may take the form of tablets, pills, capsules, semisolids, powders, sustained release formulations, solutions, suspensions, elixirs, aerosols or any other suitable compositions. Another preferred method of administering the compounds of the preferred embodiments is inhalation. This is an effective method for delivering therapeutic agents directly to the respiratory tract (see, e.g., U.S. Pat. No. 5,607,915).

Suitable pharmaceutically acceptable carriers or excipients include: for example, treatment agents and drug delivery modifiers and accelerators, such as calcium phosphate, magnesium stearate, talc, monosaccharides, disaccharides, starches, gelatin, cellulose, sodium methylcellulose, carboxymethylcellulose, glucose, hydroxypropyl-B-cyclodextrin, polyvinylpyrrolidone, low melting wax, ion exchange resin and the like, and combinations of any two or more thereof. Liquid and semi-solid excipients may be selected from glycerol, propylene glycol, water, ethanol and various oils including petroleum, animal oils, vegetable oils or synthetic sources such as peanut oil, soybean oil, mineral oil, sesame oil and the like. Preferred liquid carriers, particularly carriers for injectable solutions, include water, saline, glucose aqueous solution and ethylene glycol. Other suitable pharmaceutically acceptable excipients are described in Remington's Pharmaceutical Sciences, Mack Pub. Co., New Jersey (1991), which is incorporated herein by reference.

As used herein, the phrase "pharmaceutically acceptable salt" refers to a non-toxic acid or alkaline earth metal salt of the compound of formula I. These salts can be prepared in situ at the final separation and purification of the compounds of formula I, or by reacting a suitable organic or inorganic acid or alkali with an alkaline or acidic functional group, respectively. Representative salts include, but are not limited to: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucose heptylate, glycerophosphate, hemisulfate, heptanoate, hexanoate, fumarate, hydrochloride, hydrobromide, hydriodate, 2-hydroxyethanesulfonate, lactate, maleate, methanesulfonate, nicotinate, 2-naphthyl sulfonate, oxalate, pamoate, pectate, thiocyanate, 3-phenyl propionate, picrate, pivalate, propionate, succinate, sulfate, tartrate, thiocyanate, p-toluenesulfonate and undecanoate. In addition, the N-containing basic groups can be quaternized with the following reagents: alkyl halides such as chlorides, bromides and iodides of methyl, ethyl, propyl, butyl; dialkyl sulfate such as dimethyl, diethyl, dibutyl and dipentyl sulfates; long chain halides such as chlorides, bromides and iodides of decyl, lauryl, myristyl and stearyl; aromatic alkyl halides such as benzyl and benzene ethyl bromide and the like. A water-soluble or oil-soluble or dispersible product is thereby obtained. Examples of acids which may be used to form pharmaceutically acceptable acid addition salts include inorganic acids such as hydrochloric acid, sulfuric acid, phosphoric acid, and organic acids such as oxalic acid, maleic acid, methanesulfonic acid, succinic acid and citric acid. The alkali addition salts may be prepared in situ at the time of final separation and purification of the compounds of formula I, or by reacting the carboxylic acid moieties with a suitable alkali (such as a hydroxide, carbonate or bicarbonate of a pharmaceutically acceptable metal cation), or ammonia, or an organic primary, secondary or tertiary amine, respectively. Pharmaceutically acceptable salts include, but are not limited to, salts based on cations of alkali and alkaline earth metals, such as sodium, lithium, potassium, calcium, magnesium, aluminum and the like, and non-toxic ammonium, quaternary ammonium and amine cations, including but not limited to, ammonium, tetramethylammonium, tetraethylammonium, methylamine, dimethylamine, trimethylamine, triethylamine, ethylamine and the like. Other representative organic amines used to form the alkali addition salts include diethylamine, ethylenediamine, ethanolamine, diethanolamine, piperazine and the like.

As used herein, the term "pharmaceutically acceptable prodrugs" refer to the prodrugs of the compounds of the preferred embodiments, which are compounds rapidly converted in vivo into the parent compounds represented by the above general formulas, for example, by being hydrolyzed in the blood. Full discussion was provided in "T. Higuchi and V. Stella, Pro-drugs as Novel Delivery Systems, A.C.S., Vol. 14 of 15 Symposium Series" and "Edward B. Roche, eds., Bioreversible Carriers in Drug Design, American Pharmaceutical Association and Pergamon Press, 1987", both of which are incorporated herein by reference.

The present invention will be further illustrated below with reference to specific examples. It should be understood that these examples are only to illustrate the present invention but not to limit the scope of the present invention. The experimental methods with no specific conditions described in the following examples are generally performed under conventional conditions, such as the conditions described in Sambrook et al, Molecular Cloning: the laboratory manual (New York: Cold Spring Harbor Laboratory Press, 1989), or according to the manufacture's instruction. Unless otherwise indicated, percentages and parts are by weight.

The main advantages of the present invention are:

(1) providing a structurally novel compound of formula I;

(2) the compound of the present invention can be used as an efficient IDO enzyme inhibitor;

(3) the synthesis method is mild, easy to operate, high-yielding, easy to derivatize, suitable for the scalable industrial production;

(4) the compound of the present invention possesses anti-tumor, anti-neurodegenerative diseases (Alzheimer's disease), anti-inflammatory and other pharmacological activities.

Unless otherwise defined, all the technical and scientific terms used herein are of the same meanings that are familiar to those skilled in the art. In addition, any methods and materials similar with or equivalent to those described herein can be applied to the present invention. The preferred embodiments and materials described herein are for exemplary purposes only.

EXAMPLE 1

The Preparation of (±)(Z)—N-(3-bromo-4-fluoro-phenyl-N'-hydroxy-4-((2-(thio-methyl sulfoxide imine)propyl)amino)-1,2,5-oxadiazole-3-carboxami-dine (Compound 1)

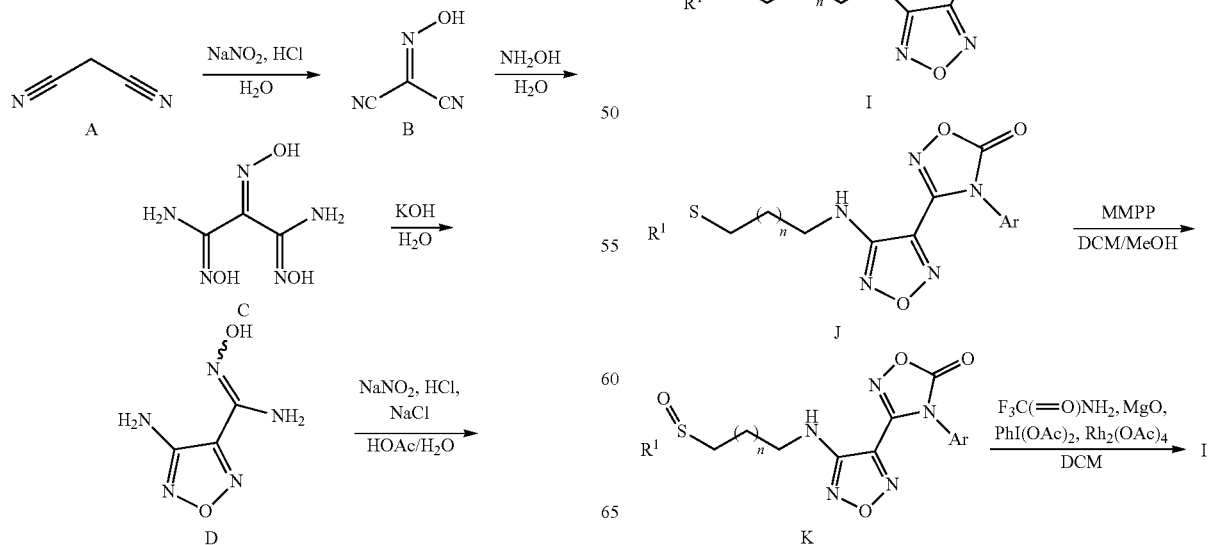

17

-continued

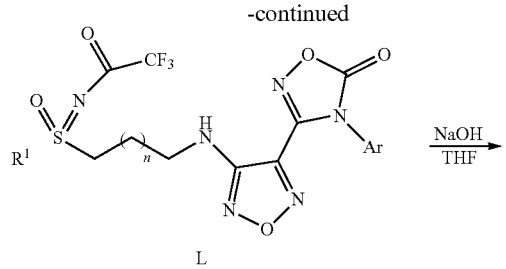

L

NaOH / THF →

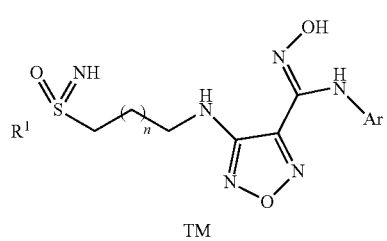

TM

Step 1: The Preparation of 4-amino-N'-hydroxy-1,2, 5-oxadiazole-3-carboxamidine (Compound D)

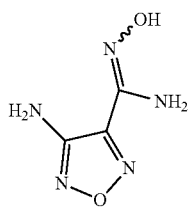

D

Propylene cyanide (3.2 g, 48.5 mmol) was dissolved in 70 mL of water and heated until completely dissolved. In ice bath, sodium nitrite (3.8 g, 55 mmol) and 6 N of hydrochloric acid (0.6 mL) were added. After the reaction was carried out in an ice bath for 0.5 hour, the temperature was raised to room temperature for 2 hours. The reaction solution was then cooled in an ice bath and 50% aqueous solution of hydroxylamine hydrochloride (9.9 g, 150 mmol) was added dropwise to the reaction solution. After stirring for half an hour, the reaction was heated to room temperature for 1 hour, and then heated to reflux for 2 hours. After the reaction was completed, the pH was adjusted to 7.0 with 8 mL of 6 N hydrochloric acid under the ice bath. The precipitate was filtered, washed once with water and ethyl acetate, respectively, and dried to give 6.0 g of white compound in a yield of 93%.

$^{13}$C NMR (75 MHz, DMSO-d$_6$): δ 154.4, 144.0, 140.0.

MS ESI: m/z=144.0, [M+H]$^+$.

18

Step 2: The Preparation of 4-amino-N-hydroxy-1,2,5-oxadiazole-3-carboxamidine chloride (Compound E)

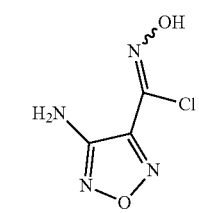

E

Compound D (4.2 g, 29.4 mmol) was dissolved in 30 mL of acetic acid and 60 mL of water, 15 mL of hydrochloric acid and sodium chloride (5.2 g, 88.2 mmol) were added, respectively. Under ice bath, sodium nitrite (2.0 g, 29.4 mmol) in 7 mL of water was dropwise added, and the reaction was maintained at 0° C. for 1 hour, and then raised to room temperature for 5 hours. After the reaction was completed, the precipitate was filtered, washed once with water and dried to give 2.6 g of a white solid compound in a yield of 55%.

$^{13}$C NMR (75 MHz, DMSO-d$_6$): δ 154.4, 142.3, 126.9.

MS ESI: m/z=160.9, [M+H]$^-$.

Step 3: The Preparation of 4-amino-N'-hydroxy-N-(2-methylthioethyl)-1,2,5-oxadiazole-3-carboxamidine (Compound F)

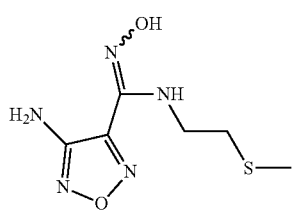

F

Compound E (2.1 g, 13.0 mmol) was dissolved in 10 mL of ethyl acetate and the 2-methylthio-1-ethylamine (1.6 mL, 14.3 mmol) was added to the reaction solution under the ice bath. After stirring for 10 minutes, triethylamine (2.7 mL, 19.5 mmol) was added and reacted for 1 hour. Extracted with ethyl acetate for 3 times, the organic layer was combined, washed once with water and once with brine, solvent was spin dried and air dried to give 2.8 g of pale yellow solid, in a yield of 93%.

$^1$H NMR (300 MHz, acetone-d$_6$): δ 9.85 (s, 1H), 6.13 (s, 1H), 5.90 (s, 2H), 3.80 (q, 2H), 2.68 (t, 2H), 2.09 (s, 3H).

Step 4: The Preparation of N'-hydroxy-4-(((2-methylthio)ethyl)amino)-1,2,5-oxadiazole-3-carboxamidine (Compound G)

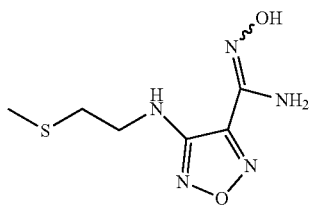

Compound F (2.4 g, 10.4 mmol) was added to 20 mL of water, and reacted with potassium hydroxide (1.8 g, 31.2 mmol) under reflux for 20 hours. Extracted with ethyl acetate for 3 times, the organic layer was combined, dried, solvent was spin dried, air dried to give 2.0 g of white crude, in a yield of 83%.

$^1$H NMR (300 MHz, acetone-$d_6$): δ 9.83 (s, 1H), 6.28 (s, 1H), 5.83 (s, 2H), 3.49 (q, 2H), 2.75 (m, 2H), 2.10 (s, 3H).

Step 5: The Preparation of N-hydroxy-4-(((2-methylthio)ethyl)amino)1,2,5-oxadiazole-3-carboxamidine chloride (Compound H)

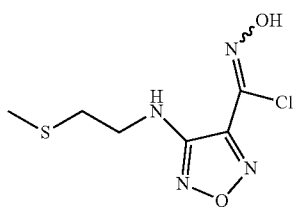

Compound G (1.0 g, 4.3 mmol) was dissolved in 5 mL of acetic acid, and 5 mL of water, 5 mL of hydrochloric acid and sodium chloride (0.8 g, 13.2 mmol) were added respectively. Under ice bath, sodium nitrite (0.3 g, 4.3 mmol) in 7 mL of water was added dropwise, the reaction was maintained at 0° C. for 1 hour and then raised to room temperature for 5 hours. After the reaction was completed, extracted with ethyl acetate for 3 times, the organic layer was combined, washed with water and brine once, respectively. The solvent was spin dried and air dried to give 1.1 g of white solid compound in a yield of 110%.

$^1$H NMR (300 MHz, DMSO-$d_6$): δ 6.13 (t, 1H), 3.45 (q, 2H), 2.73 (t, 2H), 2.09 (s, 3H).

Step 6: The Preparation of N-(3-bromo-4-fluorophenyl)-N'-hydroxy-4-(((2-methylthio)ethyl)amino)-1,2,5-oxadiazole-3-carboxamidine (Compound I)

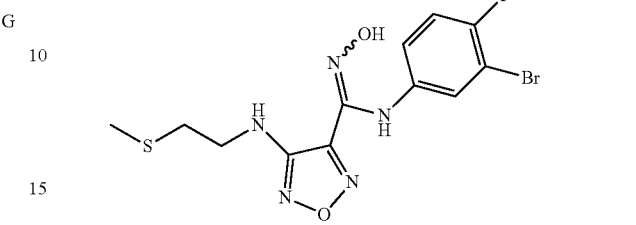

Compound H (1.0 g, 4.0 mmol) was dissolved in 3 mL of dioxane and 3 mL of water, heated to 60° C., and 3-bromo-4-fluoroaniline (0.8 g, 4.2 mmol) was added. After stirring for 10 minutes, 3 mL of aqueous sodium hydrogen carbonate was added. After 1 hour of reaction, cooled to room temperature. After the completion of the reaction, extracted with ethyl acetate for 3 times, the organic layer was combined, solvent was spin dried and air dried to give 1.5 g of yellow solid in a yield of 95%.

$^1$H NMR (300 MHz, acetone-$d_6$): δ 10.59 (s, 1H), 8.05 (s, 1H), 7.21 (s, 1H), 7.10 (t, 1H), 6.95 (s, 1H), 6.18(s, 1H), 3.48 (q, 2H), 2.73 (t, 2H), 2.05 (s, 3H).

Step 7: The Preparation of 4-(3-bromo-4-fluorophenyl)-3-4-(((2-methylthio)ethyl)amino)-1,2,5-oxadiazole-3-yl)-1,2,4-oxadiazolone (Compound J)

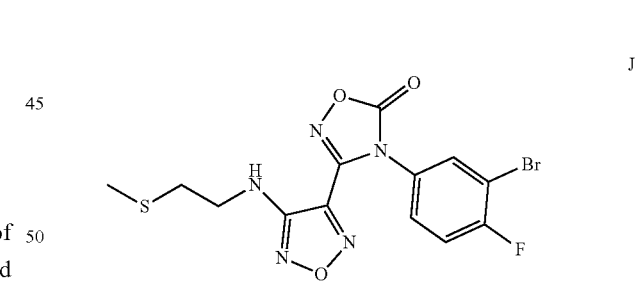

Compound I (1.0 g, 2.5 mmol) was dissolved in 10 mL of ethyl acetate, carbonyl diimidazole (0.6 g, 3.8 mmol) was added and heated to 60° C. for 1 hour. The solution was cooled to room temperature and extracted with ethyl acetate for three times. The organic layer was combined and the solvent was spin dried and air dried to give 1.1 g of yellow solid in a yield of 99%.

$^1$H NMR (300 MHz, acetone-$d_6$): δ 8.08 (d, 1H), 7.80(dd, 1H), 7.57 (t, 1H), 6.14 (s, 1H), 3.66 (q, 2H), 2.78-2.84 (m, 2H), 2.13 (s, 3H).

Step 8: The Preparation of (±)4-(3-bromo-4-fluoro-phenyl)3-4-(((2-(methyl sulfoxide)ethyl)amino)-1,2, 5-oxadiazole-3-yl)-1,2,4-oxadiazolone (Compound K)

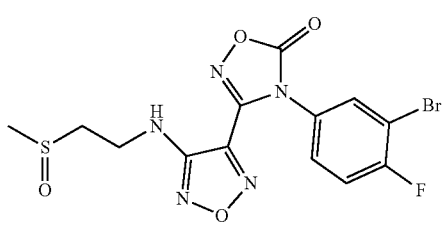

Compound J (0.8 g, 1.9 mmol) was dissolved in 11 mL (dichloromethane:methanol=10:1) and MMPP (0.5 g, 1.0 mmol) was added and reacted at room temperature for 4 hours. After the completion of the reaction, extracted with ethyl acetate for three times. The organic layer was combined, the solvent was spin dried and air dried to give 0.7 g of yellow solid in a yield of 88%.

$^1$H NMR (300 MHz, acetone-$d_6$): δ 8.08 (dd, 1H), 7.75-7.81 (m, 1H), 7.54 (t, 1H), 6.41 (s, 1H), 3.80-3.89 (m, 2H), 2.96-3.02 (m, 1H), 3.04-2.91 (m, 1H), 2.63 (s, 3H).

Step 9: The Preparation of (±)4-(3-bromo-4-fluoro-phenyl)3-4-(((2-(methyl trifluoroacetyl sulfoxide imine)ethyl)amino)-1,2,5-oxadiazole-3-yl)-1,2,4-oxadiazolone (Compound L)

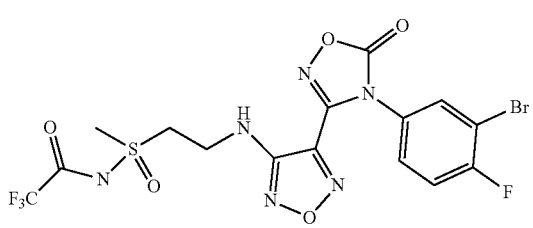

Compound K (0.5 g, 1.1 mmol), trifluoroacetamide (0.3 g, 2.2 mmol), magnesium oxide (0.2 g, 4.8 mmol) and rhodium acetate (catalytic amount) were dissolved in 2 mL of methylene chloride solution, iodobenzene acetate (0.6 mg, 1.7 mmol) was added and stirred at room temperature overnight. The reaction mixture was filtered, mother liquor was spin dried, and water was added, extracted with ethyl acetate for 3 times. The organic layer was combined, the solvent was spin dried and air dried to give 0.5 g of crude product in a yield of 97%.

$^1$H NMR (500 MHz, acetone-$d_6$): δ 8.07 (dd, 1H), 7.78 (ddd, 1H), 7.55 (t, 1H), 6.49 (s, 1H), 4.04-4.14 (m, 4H), 3.67 (s, 3H).

Step 10: The Preparation of (±) (Z)—N-(3-bromo-4-fluorophenyl)-N'-hydroxy-4-((2-(thio-methyl sulfoxide imine)ethyl)amino)-1,2,5-oxadiazole-3-carboxamidine (Compound 1)

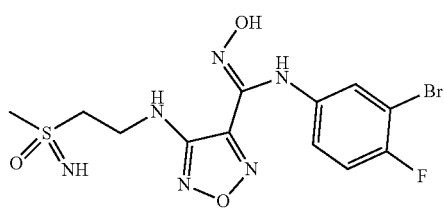

Compound L (0.5 g, 1.1 mmol) was dissolved in 2 mL of tetrahydrofuran, 0.5 mL of 2N sodium hydroxide solution was added, and reacted at room temperature for 1 hour. The solvent was spin dried. Extracted with ethyl acetate for 3 times, the organic layer was combined, the solvent was spin dried, recrystallized with 33% ethanol solution, dried to give 0.3 g of white solid in a yield of 71%.

$^1$H NMR (500 MHz, acetone-$d_6$): δ 7.29 (dd, 1H), 7.16 (t, 1H), 7.01 (ddd, 1H), 6.70 (s, 1H), 3.83 (q, 2H), 3.51-3.54 (m, 2H), 3.07 (s, 3H);

MS ESI: m/z=420.9, [M+H]$^+$.

EXAMPLE 2

Separation of Chiral Isomers

UltiMate3000 Standard Liquid Chromatograph for Chiral Separation

Chiral column: DAICEL ID3, 0.46×15 cm, 3 μM; flow rate 0.7 mL/min; detection wavelength: 254 nm; collection of a single enantiomer; eluent (n-hexane:isopropanol:diethylamine=70:30:0.1, volume ratio).

The compound L: (±)4-(3-bromo-4-fluorophenyl)3-4-(((2-(methyl trifluoroacetyl sulfoxide imine)ethyl)amino)-1,2,5-oxadiazole-3-yl)-1,2,4-oxadiazolone (60 mg) was dissolved in 1.5 mL of methylene chloride solution and injected once every 17 min. The samples were collected at 7 min and 9 min, respectively, and the isomers were 20 mg and 17 mg, respectively.

The compound was hydrolyzed and ring-opened by the method of step 10 of Example 1 to give the corresponding optical isomer 1A and isomer 1B, respectively.

EXAMPLE 3

The Preparation of (±)(Z)—N-(3-bromo-4-fluorophenyl)-N'-hydroxy-4-((3-(thio-methyl sulfoxide imine) propyl)amino)-1,2,5-oxadiazole-3-carboxamidine (Compound 2)

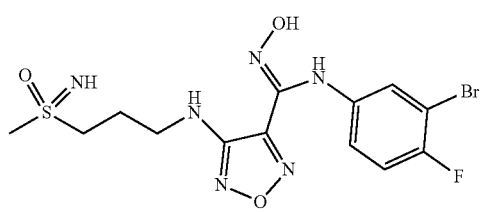

According to the preparation method of Example 1, in the third step, the compound of 3-methylthio-1-propylamine was substituted for 2-methylthio-1-ethylamine as a starting material to give compound 2.

¹HNMR (500 NMR, acetone-$d_6$): δ 10.71 (s, 1H), 8.13 (s, 1H), 7.33 (dd, J=3, 6.5 Hz, 1H), 7.21 (t, J=8.5 Hz, 1H), 7.03-7.06 (m, 1H), 6.26 (s, 1H), 3.52-3.56 (m, 2H), 3.36 (q, 7.0 Hz), 2.98 (s, 3H), 2.20-2.25 (m, 2H);

MS ESI: m/z=433.2, [M+H]⁻.

EXAMPLE 4

The Preparation of (±)(Z)—N-(3-bromo-4-fluorophenyl)-N'-hydroxy-4-((4-(thio-methyl sulfoxide imine)butyl)amino)-1,2,5-oxadiazole-3-carboxamidine (Compound 3)

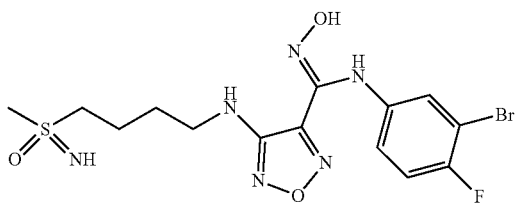

3

According to the preparation method of Example 1, in the third step, the compound of 4-methylthio-1-butylamine was substituted for 2-methylthio-1-ethylamine as a starting material to give compound 3.

¹H NMR (500 MHz, acetone-$d_6$): δ 11.19 (s, 1H), 8.10 (s, 1H), 7.28 (dd, 1H), 7.16 (t, 1H), 6.96-7.04 (m, 1H), 6.21 (t, 1H), 3.39 (q, 2H), 3.18-3.27 (m, 2H), 3.00 (s, 3H), 1.90-2.01 (m, 2H), 1.77-1.90 (m, 2H);

MS ESI: m/z=448.8, [M+H]⁺.

EXAMPLE 5

The Preparation of (±)(Z)—N-(4-fluoro-3-(trifluoromethyl)phenyl)-N'-hydroxy-4-((4-(thio-methyl sulfoxide imine)butyl)amino)-1,2,5-oxadiazole-3-carboxamidine (Compound 4)

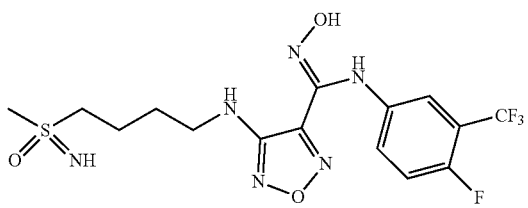

4

According to the preparation method of Example 1, in the third step, the compound of 4-methylthio-1-butylamine was substituted for 2-methylthio-1-ethylamine as a starting material to give compound 4.

¹H NMR (300 MHz, acetone-$d_6$): δ 11.08 (s, 1H), 8.29 (s, 1H), 7.33 (d, 1H), 7.28 (d, 2H), 6.20 (s, 1H), 3.38 (q, 2H), 3.20 (t, 1H), 3.13 (s, 1H), 2.96 (s, 3H), 1.92-1.94 (m, 2H), 1.83-1.86 (m, 2H);

MS ESI: m/z=438.9, [M+H]⁺.

EXAMPLE 6

The Preparation of (±)(Z)—N'-hydroxy-4-((4-(thiomethyl sulfoxide imine)butyl)amino)-N-(3-(trifluoromethyl)phenyl)-1,2,5-oxadiazole-3-carboxamidine (Compound 5)

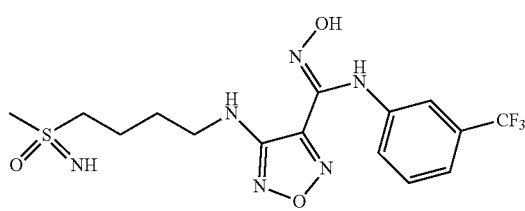

5

According to the preparation method of Example 1, in the third step, the compound of 4-methylthio-1-butylamine was substituted for 2-methylthio-1-ethylamine as a starting material; in the sixth step, 3-trifluoromethylaniline was substituted for 3-bromo-4-fluoroaniline as a starting material, to give compound 5.

¹H NMR (500 MHz, acetone-$d_6$) δ 11.35 (s, 1H), 8.28 (s, 1H), 7.46 (t, 1H), 7.29-7.32 (m, 2H), 7.19 (d, 1H), 6.22 (t, 1H), 3.40 (q, 2H), 3.22-3.25 (q, 2H), 3.22 (s, 3H), 1.90-2.02 (m, 2H), 1.84-1.87 (m, 2H);

MS ESI: m/z=420.9, [M+H]⁺.

EXAMPLE 7

The Preparation of (±)(Z)—N-(3-bromo-4-fluorophenyl)-N'-hydroxy-4-((2-(thio-methyl sulfoxide cyanoimine)ethyl)amino)-1,2,5-oxadiazole-3-carboxamidine (Compound 6)

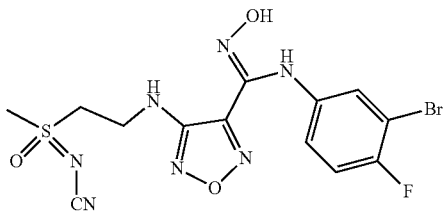

6

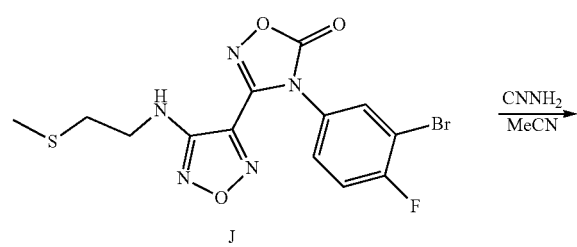

J

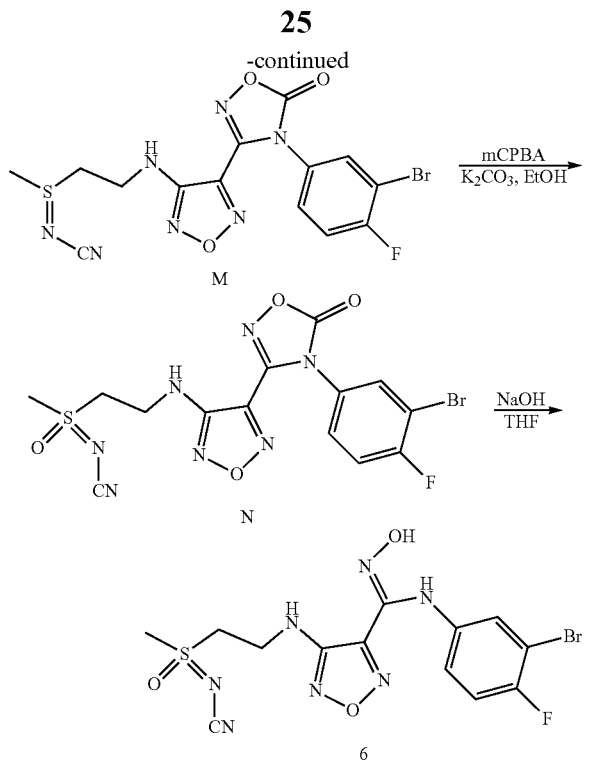

Step 1: The Preparation of (±)4-(3-bromo-4-fluorophenyl)3-4-(((2-(methyl cyano thionyl amine)ethyl)amino)-1,2,5-oxadiazole-3-yl)-1,2,4-oxadiazolone (Compound M)

According to the preparation method of Example 1, the compound J (100 mg, 0.24 mmol), cyanamide (19.8 mg, 0.47 mmol) were dissolved in 2 mL of acetonitrile, and iodobenzene acetate (85.3 mg, 0.26 mmol) was added under ice bath, the temperature was maintained for 3 hours. The reaction mixture was extracted with ethyl acetate for 3 times, the organic phase was combined, and the solvent was spin dried, purified by flash column chromatography (Eluent: dichloromethane DCM:methanol MeOH=20:1, volume ratio), to give 96 mg of white solid in a yield of 88%.

$^1$H NMR (300 MHz, acetone-$d_6$): δ 8.08 (d, 1H), 7.77-7.79 (m, 1H), 7.55 (t, 3H), 6.54 (t, 1H), 3.97(q, 1H), 3.60-3.62 (s, 1H), 3.44-3.49 (s, 1H), 2.92 (s, 1H).

Step 2: The Preparation of (±)4-(3-bromo-4-fluorophenyl)3-4-(((2-(methyl sulfoxide cyanoimine)ethyl)amino)-1,2,5-oxadiazole-3-yl)-1,2,4-oxadiazolone (Compound N)

Under ice bath, compound M (90 mg, 0.20 mmol) was dissolved in 2 mL of ethanol, anhydrous potassium carbonate (83 mg, 0.60 mmol), metachloroperbenzoic acid (52 mg, 0.30 mmol) were added and allowed to react at room temperature for 2 hours. After the reaction was completed, extracted with ethyl acetate for 3 times, the organic layer was combined, the solvent was spin dried and air dried to give 62 mg of yellow solid in a yield of 67%.

$^1$H NMR (500 MHz, acetone-$d_6$): δ 8.08 (dd, 1H), 7.54 (t, 1H), 7.39-7.44 (m, 1H), 7.25 (t, 1H), 6.25 (s, 1H), 4.00 (q, 2H), 3.75 (q, 2H), 2.83(s, 3H).

Step 3: The Preparation of (±)(Z)—N-(3-bromo-4-fluorophenyl)-N'-hydroxy-4-((2-(S-methyl sulfoxide cyanoimine)ethyl)amino)-1,2,5-oxadiazole-3-carboxamidine (Compound 6)

Compound N (62 mg, 0.13 mmol) was dissolved in 2 mL of tetrahydrofuran, 0.5 mL of 2N sodium hydroxide solution was added, and reacted at room temperature for 1 hour. The solvent was spin dried. The remainder was extracted with ethyl acetate for 3 times, the organic layer was combined, and the solvent was spin dried, recrystallized with 33% ethanol solution and dried to give 47 mg of white solid in a yield of 80%.

$^1$H NMR (500 MHz, acetone-$d_6$): δ 10.75 (s, 1H), 8.15 (s, 1H), 7.30 (dd, 1H), 7.14 (t,1H), 6.97-7.06 (m, 1H), 6.58 (s, 1H), 3.93-4.07 (m, 4H), 3.53 (s, 3H);

MS ESI: m/z=446.4, [M+H]$^+$.

The compounds prepared in Examples 3-7 can be resolved using the method of Example 2 to give the respective optical isomers.

EXAMPLE 8

Separation of Chiral Isomers

Novasep's Model 30-50 Supercritical Fluid Chromatography for Chiral Separation:

Chiral column: DAICEL CHIRALCEL OZ, 5.0×25 cm, size of fillers: 10 mM; flow rate: 140 mL/min; detection wavelength: 220 nm; collection of a single enantiomer; eluent ($CO_2$:MeOH=70:30, Volume ratio).

Conditions: compound 6, (±) (Z)—N-(3-bromo-4-fluorophenyl)-N'-hydroxy-4-((2-(thio-methyl sulfoxide cyanoimine)ethyl) amino)-1,2,5-oxadiazole-3-carboxamidine (14.99 g) (prepared as in Example 7), was dissolved in 1.5 L of methanol solution, injected once every 5 minutes, the samples were collected at 12 min and 14.8 min respectively, to give two optical isomers, the first compound was 6A (6.46 g) and the compound thereafter was 6B (6.53 g).

EXAMPLE 9

The Preparation of (±) (Z)—N-(3-bromo-4-fluorophenyl)-N'-hydroxy-4-((2-(thio-phenyl sulfoxide imine)ethyl)amino)-1,2,5-oxadiazole-3-carboxamidine (Compound 7)

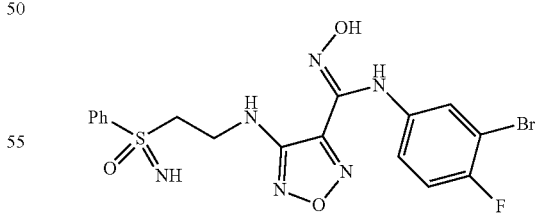

According to the preparation method of Example 1, in the third step, 4-phenylthio-1-butylamine was substituted for 2-methylthio-1-ethylamine as a starting material, to give Compound 7.

$^1$H NMR (500 MHz, acetone-$d_6$) δ: 11.0 (s, 1H), 8.20 (s, 1H), 8.10 (d, 2H), 7.61-7.80 (m, 3H), 7.30-7.32 (m, 1H), 7.20 (t, 1H), 6.92-7.03 (m, 1H), 6.70 (s. 1H), 3.72 (s, 1H), 3.61-3.70 (m, 2H), 3.5 (t, 2H);

MS ESI: m/z=485.2, [M+H]$^+$.

EXAMPLE 10

The Preparation of (±)(Z)—N-(3-pentafluoride thiophenyl)-N'-hydroxy-4-((2-(thio-methyl sulfoxide imine)ethyl)amino)-1,2,5-oxadiazole-3-carboxamidine (Compound 8)

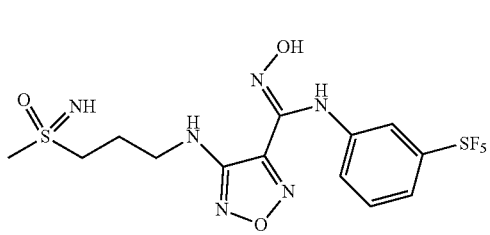

According to the preparation method of Example 1, in the third step, 3-methylthio-1-propylamine was substituted for 2-methylthio-1-ethylamine as a starting material; in the sixth step, 3-trifluoromethylaniline was substituted for 3-bromo-4-fluoroaniline as a starting material, to give Compound 8.

$^1$H NMR (500 MHz, acetone-$d_6$) δ 11.06 (s, 1H), 8.31-8.41 (m 1H), 7.92-8.03 (m, 1H), 7.38-7.44 (m, 1H), 7.10-7.19 (m, 1H), 6.18-6.26 (t, 1H), 3.49-3.54 (m, 2H), 3.09-3.22 (m, 2H), 2.97 (s, 3H), 2.85-2.97 (m, 3H), 2.05-2.24 (m, 2H);

MS ESI: m/z=465.0, [M+H]$^+$.

EXAMPLE 11

The Preparation of (±) (Z)—N-(3-bromo-4-fluorophenyl)-N'-hydroxy-4-((3-(thio-methyl sulfoxide cyano amine)propyl)amino)-1,2,5-oxadiazole-3-carboxamidine (Compound 9)

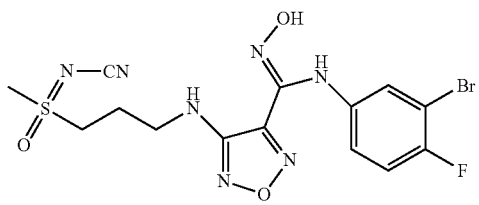

According to the preparation method of Example 1, in the third step, 3-methylthio-1-propylamine was substituted for 2-methylthio-1-ethylamine as a starting material, and then according to the preparation method of Example 7, to give compound 9.

$^1$H NMR (500 MHz, DMSO-$d_6$) δ: 8.89 (s, 1H), 7.17 (t, 1H), 7.18(t, 1H), 6.77 (t, 1H), 6.37 (t, 1H), 3.65 (t, 2H), 3.47 (s, 3H), 3.335-3.38 (m, 2H), 2.07-2.11 (m, 2H); MS ESI: m/z=461.8, [M+H]$^+$.

EXAMPLE 12

The Preparation of (±) (Z)—N-(3-chloro-4-fluorophenyl)-N'-hydroxy-4-((3-(thio-methyl sulfoxide cyano amine)propyl)amino)-1,2,5-oxadiazole-3-carboxamidine (Compound 10

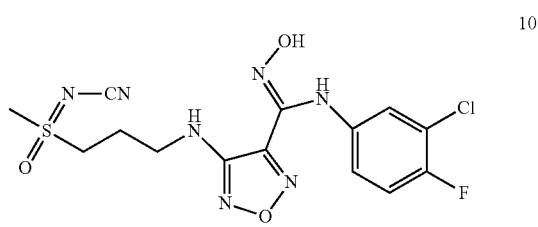 [SMILES: CS(=O)(CCCNc1nonc1/C(=N/O)Nc1ccc(F)c(Cl)c1)=NC#N]

According to the preparation method of Example 1, in the third step, 3-methylthio-1-propylamine was substituted for 2-methylthio-1-ethylamine as a starting material; in the sixth step, 3-chloro-4-fluoroaniline was substituted for 3-bromo-4-fluoroaniline as a starting material, and then according to the preparation method of Example 7, to give compound 10.

$^1$H NMR (500 MHz, DMSO-$d_6$) δ: 8.89 (s, 1H), 7.17 (t, 1H), 7.18(t, 1H), 6.77 (t, 1H), 6.37 (t, 1H), 3.65 (t, 2H), 3.47 (s, 3H), 3.35-3.38 (m, 2H), 2.07-2.11 (m, 2H);

MS ESI: m/z=415.9, [M+H]$^+$.

EXAMPLE 13

The Preparation of (±) (Z)—N-(3-bromo-4-fluorophenyl)-N'-hydroxy-4-((4-(thio-methyl sulfoxide cyano amine)butyl)amino)-1,2,5-oxadiazole-3-carboxamidine (Compound 11)

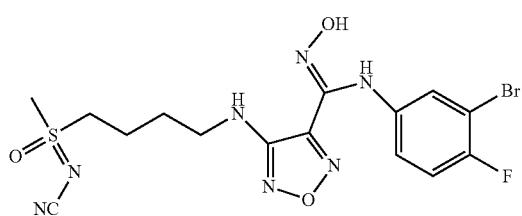

According to the preparation method of Example 1, in the third step, 4-methylthio-1-butylamine was substituted for 2-methylthio-1-ethylamine as a starting material, and then according to the preparation method of Example 7, to give compound 11.

$^1$H NMR (500 MHz, DMSO-$d_6$) δ: 8.89 (s, 1H), 7.19 (t, 1H), 7.11(t, 1H), 6.77 (t, 1H), 6.25 (t, 1H), 3.66 (t, 2H), 3.44 (s, 3H), 3.23-3.27 (m, 2H), 1.81-1.84 (m, 2H), 1.70-1.73 (m, 2H);

MS ESI: m/z=497.8, [M+Na]$^+$.

EXAMPLE 14

The Preparation of (±)(Z)—N-(3-chloro-4-fluorophenyl)-N'-hydroxy-4-((4-(thio-methyl sulfoxide cyano amine)butyl)amino)-1,2,5-oxadiazole-3-carboxamidine (Compound 12)

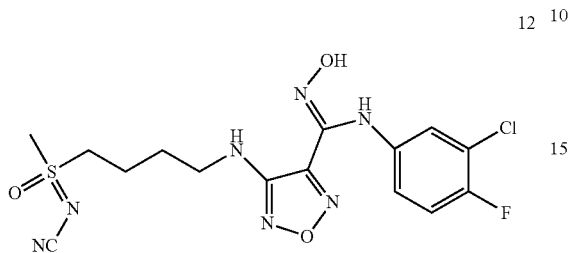

According to the preparation method of Example 1, in the third step, 4-methylthio-1-butylamine was substituted for 2-methylthio-1-ethylamine as a starting material; in the sixth step, 3-chloro-4-fluoroaniline was substituted for 3-bromo-4-fluoroaniline as a starting material, and then according to the preparation method of Example 7, to give compound 12.

$^1$H NMR (500 MHz, DMSO-d$_6$) δ: 8.89 (s, 1H), 7.19 (t, 1H), 6.94-6.96 (m, 1H), 6.77 (t, 1H), 6.25 (t, 1H), 3.66 (t, 2H), 3.42 (s, 3H), 3.20-3.24 (m, 2H), 1.77-1.79 (m, 2H), 1.66-1.70 (m, 2H);
MS ESI: m/z=429.9, [M+Na]$^+$.

EXAMPLE 15

The Preparation of (±) (Z)—N-(3-bromo-4-fluorophenyl)-N'-hydroxy(thio-methyl sulfoxide cyano amine)ethyl)amino)-1,2,5-oxadiazole-3-(2,2-dimethyl) butyrate (Compound 13)

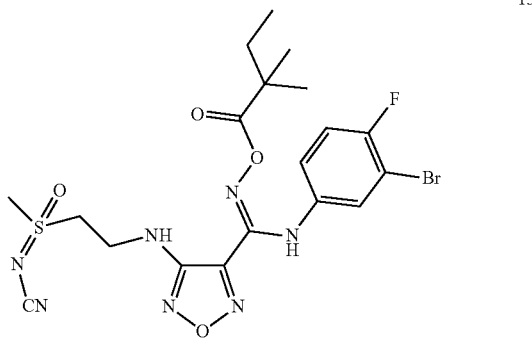

Compound 6 (50 mg, 0.11 mmol) was dissolved into 2 mL of DMF, 3,3-dimethyl butyric acid (13 mg, 0.11 mmol), EDCI (43 mg, 0.22 mmol), HOBt (30 mg, 0.22 mmol), triethylamine (34 mg, 0.34 mmol) were added. After the reaction was completed, 10 mL of water was added, and extracted with ethyl acetate for 3 times, the organic layer was combined, the solvent was spin dried, and air dried to give 50 mg of yellow solid in a yield of 82%.

$^1$H NMR (500 MHz, MeOD-d$_4$) δ: 7.40 (d, 1H), 7.14-7.18 (m, 1H), 7.11 (s, 1H), 4.58 (s, 2H), 3.96-3.93 (m, 4H), 3.47 (s, 3H), 1.36-1.30 (m, 2H), 0.98 (s, 6H), 0.79 (t, 3H);
MS ESI: m/z=544.1, [M+H]$^+$.

EXAMPLE 16

The Preparation of (±)(Z)—N-(3-Br-4-fluorophenyl)-N'-hydroxy-4-((2-(thio-methyl sulfoxide cyano amine) ethyl) amino)-1,2,5-oxadiazole-3-isobutyrate (Compound 14)

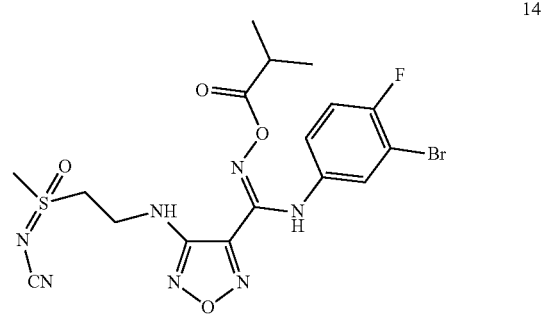 [SMILES: CC(C)C(=O)O/N=C(\Nc1ccc(F)c(Br)c1)c1nonc1NCCS(C)(=O)=NC#N]

Compound 6 (50 mg, 0.11 mmol) was dissolved into 2 mL of DMF, isopropionic acid (10 mg, 0.11 mmol), EDCI (43 mg, 0.22 mmol), HOBt (30 mg, 0.22 mmol), triethylamine (34 mg, 0.34 mmol) were added. After the reaction was completed, 10 mL of water was added, and extracted with ethyl acetate for 3 times, the organic layer was combined, the solvent was spin dried, and air dried to give 50 mg of yellow solid in a yield of 87%.

$^1$H NMR (500 MHz, MeOD-d$_4$) δ: 7.39 (d, 1H), 7.19 (t, 1H), 7.07-7.11 (m, 1H), 3.95 (s, 4H), 3.42 (s, 3H), 2.49-2.58(m, 1H); 1.10 (s, 6H);
MS ESI: m/z=516.1, [M+H]$^+$.

EXAMPLE 17

The Preparation of (±)(Z)—N-(3-bromo-4-fluorophenyl)-N'-hydroxy-4-((2-(thio-methyl sulfoxide cyano amine)ethyl)amino)-1,2,5-oxadiazole-3-trimethyl acetate (Compound 15)

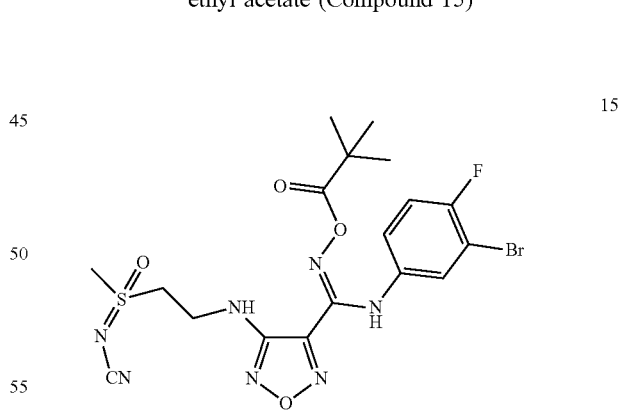

Compound 6 (100 mg, 0.22 mmol) was dissolved into 2 mL of DMF, and t-butyric acid (23 mg, 0.22 mmol), 1-ethyl-(3-dimethylaminopropyl) carbodiimide hydrochloride (EDCl) (76 mg, 0.45 mmol), 1-hydroxybenzotriazole (HOBt) (61 mg, 0.45 mmol), triethylamine (68 mg, 0.68 mmol) were added. After the reaction was completed, 10 mL of water was added, and extracted with ethyl acetate for 3 times, the organic layer was combined, the solvent was spin dried, and air dried to give 100 mg of yellow solid in a yield of 86%.

$^1$H NMR (500 MHz, MeOD-d$_4$) δ: 7.39 (d, 1H), 7.11-7.13 (m, 2H), 7.07 (s, 1H), 6.79-6.82 (m, 1H); 3.99-4.02 (m, 2H), 3.73-3.82 (m, 2H), 3.36 (s, 3H), 1.05 (s, 9H);

MS ESI: m/z=530.1, [M+H]$^+$.

The compounds prepared by all the Examples can be resolved using the method of Example 2 or 8 to give the respective optical isomers.

EXAMPLE 18

Activity Test (1) The Induced Expression and Purification Method for the IDO Protein Firstly, the IDO gene was amplified by PCR, the PCR amplification products were recovered, and then the pET28a plasmid (purchased from Shanghai Baoman Biotechnology Co., Ltd.) and the IDO gel recovery products were digested with EcoR I and Xho I restriction endonucleases (37° C., digestion for 2 h), electrophorized and recovered. The recovered products were ligated overnight by a T4 ligase and then the ligation products were added to DH5α competent cells, placed on ice for 30 min, heat-shocked at 42° C. for 90 s, cultured on a shaker, and seeded to a plate. Monoclonies were picked, identified by PCR and then by sequencing. All sequences were correct, meaning the construction of pET28a-IDO plasmid was successful.

The constructed BL21 containing the pET28a-IDO plasmid was cultured at 37° C. to OD$_{600}$=0.6-0.8, and a final concentration of 7 μM of chlorine methemoglobin and 1 mM of IPTG (isopropyl-β-D-thiogalactoside) were added for induction at 28° C. for 4 h; after the induction, the cell was centrifuged at 6000 rpm at 4° C., the collected cells were washed once with 20 mM PBS (pH6.5), and centrifuged and collected again.

The collected cells were resuspended with a lysis solution (20 mM PBS pH 6.5), ultrasonically lysed (40% of power, lysis for 20 min, placed on ice), the lysed bacteria were centrifuged at 13000 rpm for 15 min, precipitate was discarded and the supernatant was maintained; the nickel column was equilibrated with the lysis solution (20 mM PBS pH 6.5) for 3 column volumes, and then the lysis supernatant was loaded onto the nickel column; after loading, four column volumes of a rinsing solution (20 mM PBS pH 6.5, 20 mM imidazole) were used for washing, and finally protein was eluted with eluent (20 mM PBS pH 6.5, 250 mM imidazole); the eluted protein solution was dialyzed for 4 h, and the dialysis solution was 20 mM PBS, pH 6.5. After the dialysis, the protein sample was concentrated, packed, flash frozen by liquid nitrogen, and stored at −80° C. for further use.

(2) Test Method for IDO Enzyme Inhibitory Activity

Firstly, the compound was subject to a 3-fold gradient dilution. 1 μL of each concentration was added to a 96-well plate; 50 μL of the IDO enzyme solution (final concentration 600 ng/100μL) was added: 25 μL of substrate 1 mixture solution was added, 25 μL of substrate 2 mixture solution was added to initiate the reaction. Finally, the plate was read at OD321 nm, 60 min.

(3) Test Method for Cell Activity

Hela cells (100 μL) were inoculated on a 96-well plate at an inoculation amount of 5×10$^3$ per well and grown overnight. The next day, after the compound was diluted, 1 μL was added to a 96-well plate and then 100 μL of medium containing human interferon y (final concentration of 50 ng/mL) was added to the 96-well plate to allow the final volume to be 200 μL. 48 h after incubating, 140 μL of supernatant in each well was transferred to a new 96-well plate. 10 μL of 6.1 N trichloroacetic acid was added to each well and mixed and incubated at 50° C. for 30 min, IDO catalyzed N-formyl canine urea to become canine urea. The reaction mixture was centrifuged at 2500 rpm for 10 minutes to remove the precipitate. 100 μL of supernatant in each well was transferred to a new 96-well plate and mixed with 100 μL of 2% dimethylaminobenzaldehyde acetic acid solution. After the canine urea was separated, the value was measured at 480 nm using a SPECTRAmax i3 reader.

The test result of IDO enzyme inhibitory activity and cell inhibitory activity for each compound is shown in Table 1.

TABLE 1

Test result of IDO enzyme and cell inhibitory activity

| Compound No. | IDO IC$_{50}$ (μM) | Hela IC$_{50}$ (μM) |
|---|---|---|
| compound 1 | 0.022 | 0.040 |
| compound 1A | <5.6 | <0.070 |
| compound 1B | <5.2 | <0.080 |
| compound 2 | <3 | <0.1 |
| compound 3 | 0.074 | 0.008 |
| compound 4 | <19 | <0.5 |
| compound 5 | <3.6 | <0.076 |
| compound 6 | 0.011 | 0.0018 |
| compound 6A | <0.088 | 0.0003 |
| compound 6B | <0.082 | 0.0006 |
| compound 7 | <2.6 | <0.26 |
| compound 8 | <14 | <0.8 |
| compound 9 | 0.035 | 0.0047 |
| compound 10 | <5 | 0.0028 |
| compound 11 | 0.055 | 0.0076 |
| compound 12 | <18 | 0.0028 |
| compound 13 | 0.18 | 0.014 |
| compound 14 | 0.12 | 0.0022 |
| compound 15 | 0.36 | 0.047 |
| 5-phenyl-1-imidazole(control) | 39 | >50 |

The above results demonstrate that the compounds of the present invention (including racemates and enantiomers) have excellent inhibitory activity against IDO enzymes and cells.

EXAMPLE 19

In Vivo Pharmacodynamic Test on the Growth of Colon Cancer CT26 Transplanted Tumor in Mice Under a sterile condition, CT26 cells were harvested in the proliferative phase, and the cell concentration was adjusted after digestion. The cells were inoculated under the right armpit of mice, and each inoculated volume was 0.1 mL (tumor cells 3×10$^5$). 24 hours after inoculation, 30 tumor-loaded mice were randomly divided into 5 groups according to their weight. Each group was administered according to the following regime. The day of administration was recorded as d1; the negative control group was administered the same amount of vehicle; the positive control group was INCB24360. The long and short diameters of tumor were measured twice a week.

The result is shown in Table 2.

TABLE 2

| animal group | compound | number of animals/ group | dosage (mg/kg) | volume of administration (ml/kg) | administration route | administration times/day |
| --- | --- | --- | --- | --- | --- | --- |
| 1 | Vehicle | 6 | NA | 10 | intragastric | 2 times × 14 day |
| 2 | INCB24360 | 6 | 30 | 10 | intragastric | 2 times × 14 day |
| 3 | INCB24360 | 6 | 100 | 10 | intragastric | 2 times × 14 day |
| 4 | compound 6 | 6 | 30 | 10 | intragastric | 2 times × 14 day |
| 5 | compound 6 | 6 | 100 | 10 | intragastric | 2 times × 14 day |

The inhibitory effect of compound 6 on tumor growth is shown in FIG. 1. The results show that compound 6 of the present invention has a more effective inhibitory effect on tumor growth in the mouse primary rectal cancer tumor CT-26 model than the control INCB24360.

EXAMPLE 20

The Pharmacokinetic Data of Compound 6 in Rats

1. Administration Regime

6 SD rats, male, weight 180-200 g, intragastric or intravenous administration of compound 6 (Table 3):

TABLE 3

| group | animal number | compound | administration route | administration dosage (mg/kg) | volume of administration (ml/kg) |
| --- | --- | --- | --- | --- | --- |
| 1 | 3 | 6 | intragastric | 10 | 10 |
| 2 | 3 | 6 | intravenous | 1 | 1 |

For intragastric administration, the compound was formulated into a suspension with 1% MC, and for intravenous injection the compound was formulated with DMSO: 20% PEG400 (5:95). Fasting for 12 hours before the test, free drinking water. The rats were all fed 2 hours after administration.

2. Blood Sampling Time Point and Sample Treatment:

Intragastric administration: 0.25, 0.5, 1.0, 2.0, 4.0, 6.0, 8.0 and 24 h after administration;

Intravenous administration: 5 min, 0.25, 0.5, 1.0, 2.0, 4.0, 6.0, 8.0 and 24 h after administration;

At the above set point, the venous blood was taken from the posterior venous plexus of the rat eyes, and placed in a EDTA-2K tube, centrifuged at 11000 rpm for 5 min, the plasma was separated and frozen in a −20° C. refrigerator.

3. Sample Testing and Data Analysis

The concentration of compound 6 in rat plasma was determined by LC/MS/MS.

Pharmacokinetic parameters after administration were calculated using the non-compartmental model of the Win-Nonlin 5.3 software (Pharsight, USA).

Peak concentration $C_{max}$ and peak time $T_{max}$ are measured value;

Drug area under the curve $AUC_{0-t}$ value: using trapezoidal method; $AUC_{0-\infty} = AUC_{0-t} + C_t/k_e$, $C_t$ is the blood concentration at the last measurable time point, $k_e$ is the elimination rate constant;

Elimination half-life $t_{1/2} = 0.693/k_e$;

Mean residence time MRT=AUMC/AUC.

Clearance rate $CL = D/AUC_{0-\infty}$;

Steady state distribution volume Vss=CL×MRT

Absolute Bioavailability $F = (AUC_{intragastric} \times D_{intravenous}) / (AUC_{intravenous} \times D_{intragastric}) \times 100\%$ 4. Test Results After the rats were intragastrically administered 10 mg/kg of compound 6, and intravenously administered 1 mg/kg of compound 6, the pharmacokinetic parameters are shown in Table 4 and Table 5.

TABLE 4

The pharmacokinetic parameters after the rats were intragastrically administered 10 mg/kg of compound 6

| rats NO. | $T_{max}$ (h) | $C_{max}$ (ng/mL) | $AUC_{0-t}$ (ng·h/mL) | $AUC_{0-\infty}$ (ng·h/mL) | MRT (h) | $t_{1/2}$ (h) | F (%) |
| --- | --- | --- | --- | --- | --- | --- | --- |
| 1 | 2.00 | 593 | 2341 | 2475 | 3.35 | 1.58 | |
| 2 | 1.00 | 854 | 2817 | 3007 | 3.27 | 1.80 | |
| 3 | 1.00 | 659 | 2795 | 3008 | 3.47 | 1.80 | |
| mean | 1.33 | 702 | 2651 | 2830 | 3.36 | 1.73 | 49.8 |
| standard deviation | 0.577 | 136 | 268 | 308 | 0.0970 | 0.126 | |
| CV % | 43.3 | 19.3 | 10.1 | 10.9 | 2.90 | 7.30 | |

TABLE 5

The pharmacokinetic parameters after the rats were intravenously administered 1 mg/kg of compound 6

| rats No. | $AUC_{0-t}$ (ng·h/mL) | $AUC_{0-\infty}$ (ng·h/mL) | MRT (h) | $t_{1/2}$ (h) | CL (L/h/kg) | $V_{ss}$ (L/kg) |
| --- | --- | --- | --- | --- | --- | --- |
| 5 | 546 | 563 | 1.91 | 1.71 | 1.78 | 3.39 |
| 6 | 505 | 534 | 2.03 | 2.51 | 1.87 | 3.79 |
| 7 | 547 | 555 | 1.67 | 1.32 | 1.80 | 3.02 |

TABLE 5-continued

The pharmacokinetic parameters after the rats were intravenously administered 1 mg/kg of compound 6

| rats No. | $AUC_{0-t}$ (ng · h/mL) | $AUC_{0-\infty}$ (ng · h/mL) | MRT (h) | $t_{1/2}$ (h) | CL (L/h/kg) | $V_{ss}$ (L/kg) |
|---|---|---|---|---|---|---|
| mean | 533 | 551 | 1.87 | 1.85 | 1.82 | 3.40 |
| standard deviation | 24.0 | 14.8 | 0.180 | 0.606 | 0.0492 | 0.388 |
| CV % | 4.50 | 2.70 | 9.60 | 32.8 | 2.70 | 11.4 |

The results show that after intravenous administration, the clearance rate (CL) of compound 6 in rats was 1.82 L/h/kg, the steady state distribution volume (Vss) was 3.40 L/kg and the exposure amount ($AUC_{0-t}$) was 533 ng·h/mL. After intragastric administration, the plasma peak time $T_{max}$ in rats was 1.33 h, the exposure amount (AUC0-t) was 2651 ng·h/mL, and the absolute bioavailability was 49.8% after the dosage was normalized.

EXAMPLE 21

The Pharmacokinetic Data of Compound 13 (Prodrug of Compound 6) in Rats

1. Experimental Purpose

Compound 13 was orally administered to ICR mice. Blood samples were collected at different time points. LC-MS/MS was used to determine the concentration of compound 6 in the plasma of mice after administration of the test substance, and the relevant pharmacokinetic parameters were calculated, the the pharmacological properties of compound 6 in mice was investigated.

2. Test Methods

Same with Example 20.

3. Animal Experiment

Experimental design: 3 ICR mice, provided by Suzhou Zhaoyan New Drug Research and Development Co., Ltd.; the experiment was carried out according to Table 6.

TABLE 6 administration information

| animal numbers male | test substance | numbering of animals | dosage (mg/kg) | concentration of administration (mg/mL) | volume of administration (mL/kg) | samples | mode of administration | vehicle |
|---|---|---|---|---|---|---|---|---|
| 3 | compound 13 | Mice-1 Mice-2 Mice-3 | 30.0 | 3.00 | 10.0 | plasma | PO | 50% PEG400: 50% Water |

Sample Collection

Each animal was anesthetized with isoflurane and thereafter about 25 μL of blood was collected through the eyepit, anticoagulated with EDTAK2, the collecting time points were: before administration of the test substance (0 hr) and 15 min, 30 min, 1 h, 2 h, 4 h, 6 h, 8 h and 24 h after administration of the test substance. Blood samples were collected and placed on ice and the plasma was centrifuged and separated within 1 hour (centrifugal conditions: 5000 rpm, 10 minutes, 4° C.). The collected plasma was stored at −20° C. before analysis.

4. Data Processing

Data acquisition and control system software was the Analyst1.5.1 software (Applied Biosystem). The sample peak integral method was automatic integration; The ratio of the peak area of the sample and the peak area of the internal standard was taken as the index and the concentration of the sample was regressed. Regression method: linear regression, the weight coefficient was $1/X^2$. Pharmacokinetic parameters were analyzed with a non-compartmental model using WinNonlin Professional v6.3 (Pharsight, USA). $C_{max}$ is the measured maximum blood concentration, and the area under the blood concentration-time curve $AUC_{(0 \rightarrow t)}$ was calculated from the trapezoidal method, and $T_{max}$ is the peak blood concentration time after administration. The experimental data is expressed as "mean±SD, n≥3" or "mean" (mean, n=2).

4. Experimental Results

After the prodrug of compound 6 (compound 13) was orally administered (dose of 30.0 mg/kg) to ICR mice, the pharmacokinetic study showed that the prodrug (compound 13) was substantially converted to compound R00038-0A03. The results of pharmacokinetic study in ICR mice showed that the average peak time for blood concentration of compound 6 in mice was 2 hr, the peak concentration was 250±21.9 ng/mL, $AUC_{0 \rightarrow t}$ was 2359±184 hr*ng/mL, and the mean residence time in vivo MRT was 9.76±4.64 hr.

The concentration of compound 6 in plasma at different time points is shown in Table 7 after ICR mice were administered compound 13 (PO, 30 mg/kg).

TABLE 7

The plasma solubility (ng/mL) of compound 6 after oral administration of compound 13 (30 mg/kg)

| time(hr) | Mice-1 | Mice-2 | Mice-3 | mean | SD | RSD % |
|---|---|---|---|---|---|---|
| 0.25 | 109 | 49.9 | 55.6 | 71.3 | 32.3 | 45 |
| 0.5 | 101 | 91.6 | 94.3 | 95.7 | 5.06 | 5.3 |
| 1 | 125 | 243 | 180 | 183 | 59.2 | 32 |
| 2 | 225 | 263 | 263 | 250 | 22.2 | 8.9 |
| 4 | 195 | 194 | 209 | 199 | 8.57 | 4.3 |
| 6 | 186 | 160 | 263 | 203 | 53.8 | 26 |
| 8 | 83.2 | 84.5 | 93.8 | 87.1 | 5.77 | 6.6 |
| 24 | 48.0 | 8.55 | 19.7 | 25.4 | 20.3 | 80 |

3. Calculating the Pharmacokinetic Parameters After Administration, see Pharmacokinetic Parameters According to the blood concentration data, the pharmacokinetic parameters calculated using WinNonlinV6.3 non-compartmental model are shown in Table 8.

TABLE 8

The pharmacokinetic parameters of compound 6 in ICR mice after oral administration of compound 13 (PO: 30 mg/kg)

| PK Parameters | | Mice-1 | Mice-2 | Mice-3 | Mean | SD | RSD |
|---|---|---|---|---|---|---|---|
| Dose | mg·kg$^{-1}$ | | | | 30 | | (%) |
| $K_{el}$ | L/kg | 0.0695 | 0.156 | 0.123 | 0.116 | 0.0437 | 38 |
| $t_{1/2}$ | hr | 9.97 | 4.44 | 5.63 | 6.68 | 2.91 | 44 |
| $t_{max}$ | hr | 2 | 2 | 2 | 2 | 0 | 0 |
| $C_{max}$ | ng/ml | 225 | 263 | 263 | 250 | 21.9 | 8.8 |
| $AUC_{0-t}$ | hr*ng/mL | 2391 | 2160 | 2525 | 2359 | 184 | 7.8 |
| $AUC_{0-inf}$ | hr*ng/mL | 3082 | 2215 | 2685 | 2660 | 434 | 16 |
| $AUMC_{0-t}$ | hr*hr*ng/mL | 19793 | 12189 | 16309 | 16097 | 3806 | 24 |
| $AUMC_{0-inf}$ | hr*hr*ng/mL | 46297 | 13854 | 21447 | 27199 | 16970 | 62 |
| $MRT_{PO}$ | hr | 15.0 | 6.25 | 7.99 | 9.76 | 4.64 | 48 |

The results show that the prodrug compound 13 orally administered to the mice was effectively converted into compound 6 and compound 6 has excellent pharmacokinetic parameters.

All literatures mentioned in the present application are incorporated herein by reference, as though each individually incorporated by reference. Additionally, it should be understood that after reading the above teachings, many variations and modifications may be made by the skilled in the art, and these equivalents also fall within the scope defined by the appended claims.

The invention claimed is:

1. A compound represented by formula (I), or a pharmaceutically acceptable salt, stereoisomer or tautomer, or prodrug thereof:

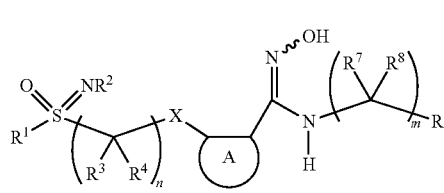

wherein, $R^7$ and $R^8$ are each independently H, substituted or unsubstituted $C_1$-$C_{10}$ alkyl, substituted or unsubstituted $C_2$-$C_{10}$ alkenyl, or substituted or unsubstituted $C_3$-$C_{10}$ alkynyl;

$R^9$ is $C_6$ aryl, optionally substituted with one or more substituents selected from the group consisting of: halogen, $C_1$-$C_6$ alkyl, hydroxy, amino, nitro, —$CF_3$, —CN, —$SF_5$, and $_{NR}{}^aR^b$; wherein each $R^a$ and each $R^b$ are each independently H, substituted or unsubstituted $C_1$-$C_{10}$ alkyl, or substituted or unsubstituted $C_2$-$C_{10}$ alkenyl, $R^2$ is H or —CN;

X is NH;

$R^3$ and $R^4$ are each independently H, or substituted or unsubstituted $C_1$-$C_{10}$ alkyl;

$R^1$ is $C_1$-$C_{10}$ alkyl, optionally substituted with one or more substituents selected from the group consisting of: halogen, hydroxy, amino, nitro, cyano, —$CF_3$, and —$SF_5$;

n is 2;

ring A is 1,2,5-oxadiazole ring; and m is 0.

2. The compound represented by formula (I) of claim 1, wherein the compound is represented by the general formula (II),

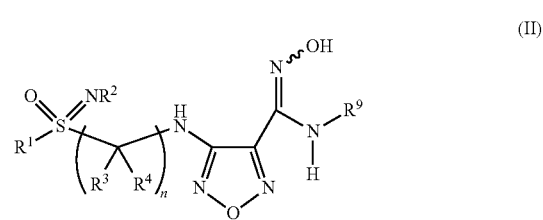

wherein, $R^9$ is $C_6$ aryl, optionally substituted with one or more substituents selected from the group consisting of: halogen, $C_1$-$C_6$ alkyl, hydroxy, amino, nitro, —$CF_3$, —CN, and —$SF_5$;

$R^3$, $R^4$, and $R^1$ are defined as in claim 1;

$R^2$ is H; and n is 2.

3. The compound represented by formula (I) of claim 2, wherein $R^1$ is $C_1$-$C_{10}$ alkyl;

$R^2$ is H;

$R^3$ and $R^4$ are each independently H; and $R^9$ is $C_6$aryl, optionally substituted with one or more substituents selected from the group consisting of: halogen and $C_1$-$C_6$ alkyl.

4. The compound represented by formula (I) of claim 3, wherein $R^1$ is $C_1$-$C_4$ alkyl;

$R^9$ is $C_6$ aryl, optionally substituted with one or more substituents selected from the group consisting of: halogen and $C_1$-$C_6$ alkyl.

5. A compound represented by formula (I), or a pharmaceutically acceptable salt, stereoisomer or tautomer, or prodrug thereof, wherein the prodrug is represented by the general formula (III),

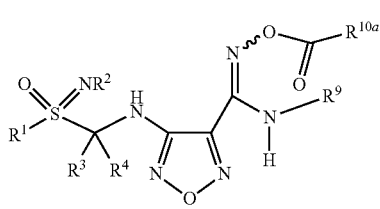

(III)

wherein,
R¹ is $C_1$-$C_{10}$ alkyl, optionally substituted with one or more substituents selected from the group consisting of: halogen, hydroxyl, amino, nitro, cyano, —$CF_3$, and —$SF_5$;
R² is H;
R³ and R⁴ are each independently H or substituted or unsubstituted $C_1$-$C_{10}$ alkyl;
R⁹ is $C_6$ aryl, optionally substituted with one or more substituents selected from the group consisting of: halogen, hydroxyl, amino, nitro, cyano, —$CF_3$, —$SF_5$ and $NR^aR^b$ wherein each $R^a$ and $R^b$ are each independently H, substituted or unsubstituted $C_1$-$C_{10}$ alkyl, or substituted or unsubstituted $C_2$-$C_{10}$ alkenyl;
$R^{10a}$ is substituted or unsubstituted $C_6$-$C_{20}$ aryl, substituted or unsubstituted five or six membered heteroaryl, substituted or unsubstituted $C_1$-$C_{12}$ alkyl, substituted or unsubstituted $C_1$-$C_{12}$ alkoxy, substituted or unsubstituted $C_3$-$C_{12}$ cycloalkyl, $C_3$-$C_{12}$ cycloalkoxy, $NR^aR^b$; wherein $R^a$ and $R^b$ are each defined as in R1 above;
wherein, said "substituted" means having one or more substituents selected from the group consisting of: halogen, hydroxy, —$NH_2$, nitro, —CN, $C_1$-$C_4$ alkyl, $C_1$-$C_4$ haloalkyl, $C_1$-$C_4$ alkoxy, $C_3$-$C_6$ cycloalkyl, $C_2$-$C_4$ alkenyl, $C_2$-$C_4$ alkynyl, phenyl and benzyl.

6. The compound represented by formula (I) of claim 1, wherein the compound is
(±)(Z)—N-(3-bromo-4-fluorophenyl)-N'-hydroxy-4-((2-(thio-methyl sulfoxide imine) ethyl)amino)-1,2,5-oxadiazole-3-carboxamidine;
(+)(Z)—N-(3-bromo-4-fluorophenyl)-N'-hydroxy-4-((2-(thio-methyl sulfoxide imine) ethyl)amino)-1,2,5-oxadiazole-3-carboxamidine; or
(−) (Z)—N-(3-bromo-4-fluorophenyl)-N'-hydroxy-4-((2-(thio-methyl sulfoxide imine) ethyl)amino)-1,2,5-oxadiazole-3-carboxamidine.

7. The compound represented by formula (I) of claim 1, wherein the pharmaceutically acceptable salt is selected from the group consisting of: hydrochloride, hydrobromide, sulfates, phosphates, methanesulfonates, trifluoromethanesulfonates, benzenesulfonates, p-toluenesulfonates, 1-naphthalenesulfonate, 2-naphthalenesulfonate, acetate, trifluoroacetate, malate, tartrate, citrate, lactate, oxalate, succinate, fumarate, maleate , benzoate, salicylate, phenylacetate, and mandelate.

8. A method for preparing the compound of formula I according to claim 1, wherein the method comprises the following steps:

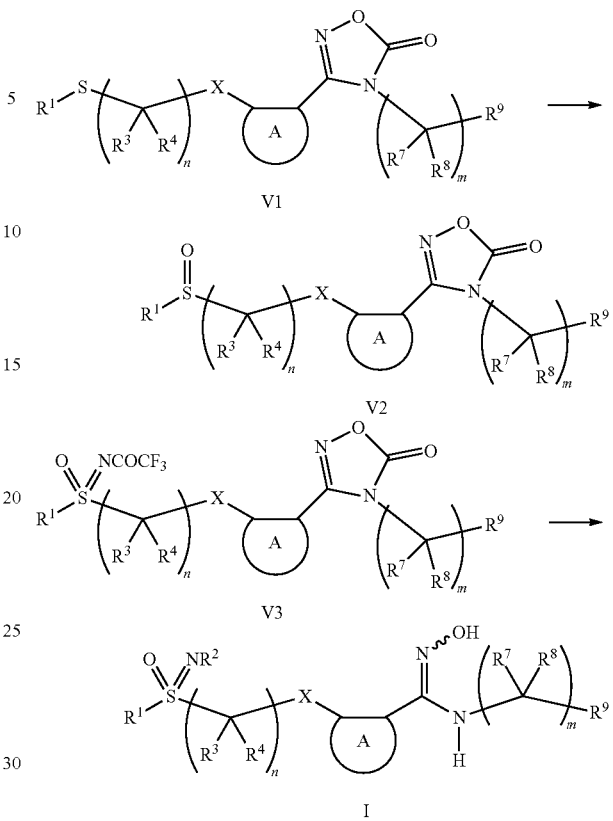

(a) reacting compound V1 with a peroxide, magnesium monoperoxyphthalate (MMPP), to obtain compound V2;
(b) reacting compound V2 with trifluoroacetamide, to obtain compound V3;
(c) in the presence of aqueous sodium hydroxide, subjecting compound V3 to a ring-open reaction, and meantime removing the trifluoroacetylamino group, to obtain the final product, i.e., the compound of formula I,
wherein, R¹, R², R³, R⁴, R⁷, R⁸, R⁹, n, m, X and ring A are defined as in claim 1.

9. A method for the treatment of an indoleamine-2,3-dioxygenase-mediated disease, comprising administering to a patient the compound of formula I according to claim 1, wherein the indoleamine-2,3-dioxygenase-mediated disease is cancer, a neurodegenerative disease, an eye disease, a psychological disorder, an anxiety disorder, and/or an autoimmune disease.

10. A pharmaceutical composition comprising:
the compound represented by formula (I), or a pharmaceutically acceptable salt, stereoisomer or tautomer, or prodrug thereof according to claim 1; and
a pharmaceutically acceptable carrier and/or an antineoplastic agent.

* * * * *